(12) United States Patent
Omura et al.

(10) Patent No.: US 7,630,836 B2
(45) Date of Patent: Dec. 8, 2009

(54) POLYNUCLEOTIDES

(75) Inventors: Satoshi Omura, Tokyo (JP); Haruo Ikeda, Kawasaki (JP); Jun Ishikawa, Sagamihara (JP); Hiroshi Horikawa, Tokyo (JP); Tadayoshi Shiba, Musashino (JP); Yoshiyuki Sakaki, Yokohama (JP); Masahira Hattori, Fuchu (JP)

(73) Assignees: The Kitasato Institute, Tokyo (JP); National Institute of Technology and Evaluation, Tokyo (JP)

( * ) Notice: Subject to any disclaimer, the term of this patent is extended or adjusted under 35 U.S.C. 154(b) by 60 days.

(21) Appl. No.: 10/156,761

(22) Filed: May 29, 2002

(65) Prior Publication Data

US 2003/0119018 A1    Jun. 26, 2003

(30) Foreign Application Priority Data

May 30, 2001 (JP) ............................. 2001-204089
Aug. 2, 2001 (JP) .......................... P.2001-272697

(51) Int. Cl.
*G01N 33/48* (2006.01)
(52) U.S. Cl. ....................................................... 702/19
(58) Field of Classification Search ..................... 435/6, 435/91.1, 486, 252.35; 536/24.3, 25.3, 23.1; 702/19, 20; 703/11; 424/93.43
See application file for complete search history.

(56) References Cited

U.S. PATENT DOCUMENTS 5,795,714 A * 8/1998 Cantor et al. .................. 435/6
6,251,636 B1 * 6/2001 Betlach et al. ................ 435/76

FOREIGN PATENT DOCUMENTS

| EP | 0 997 528 A1 | 5/2000 |
| WO | WO 99/41389 | 8/1999 |
| WO | WO 01/09155 A1 | 2/2001 |

OTHER PUBLICATIONS

Aparicio et al., "The Biosynthetic Gene Cluster for the 26-Membered Ring Polyene Macrolide Pimaricin", Apr. 1999, The Journal of Biological Chemistry, vol. 274, No. 15, pp. 10133-10139.*
GenBank Accession No. AJ132222 (GI:4678702), "*Streptomyces natalensis* pimS1 gene", Apr. 24, 1999, [online] [retrieved on Aug.

27, 2004]. <URL:http://www.ncbi.nlm.nih.gov/entrez/viewer.fcgi?db=nucleotide&val=4678702>.*
"*S. griseus* afsA gene encoding a possible A-factor biosynthesis protein", EMBL, Database accession No. SGAFSAA, Jul. 6, 1989.
"*Streptomyces fradiae* tylosin-biosynthetic regulatory gene cluster", EMBL, Database accession No. AF145049, Jun. 30, 1999.
"Gamma-butyrolactone receptor protein TyIP from *Streptomyces fradiae*", UNIPROT, Database accession No. Q9XCC7, Nov. 1, 1999.
"*S. coelicolor* putative sodium-coupled permease", UNIPROT, Database accession No. Q9KZY9, Oct. 1, 2000.
"Polypeptide involved in the biosynthesis of streptogramins", EMBL, Database accession No. AR124150, May 20, 2001.
"*Streptomyces pristinaespiralis* autoregulator receptor protein", UNIPROT, Database accession No. Q8VVP1, Mar. 1, 2002.
NCBI, Accession No. NP 821594, Apr. 13, 2006.
NCBI, Accession No. AJ 132221, Apr. 15, 2005.
NCBI, Accession No. AJ 132222, Apr. 15, 2005.
Kunst et al, "The complete genome sequence of the Gram-positive bacterium *Bacillus subtilis*", Nature, 390, 249-256 (1997).
Wang et al, "Large-Scale Identification, Mapping, and Genotyping of Single-Nucleotide Polymorphisms in the Human Genome", Science, 280, 1077-1082 (1998).
DeRisi et al, "Exploring the Metabolic and Genetic Control of Gene Expression on a Genomic Scale", Science, 278, 680-686 (1997).
Wilson et al, "Exploring drug-induced alternations in gene expression in *Mycobacterium tuberculosis* by microarray hybridization", Proc. Natl. Acad. Sci. USA, 96, 12833-12838 (1999).
Behr et al, "Comparative Genomics of BCG Vaccines by Whole-Genome DNA Microarray", Science, 284, 1520-1523 (1999).
Lockhart et al, "Expression monitoring by hybridization to high-density oligonucleotide arrays", Nature Biotechnology, 14, 1675-1680 (1996).
Ikeda et al, "Organization of the biosynthetic gene cluster for the polyketide anthelmintic macrolide avermectin in *Streptomyces avermitilis*", Proc. Natl. Acad. Sci. USA, 96, 9509-9514 (1999).
Omura, Satoshi et al, Structure prediction of secondary metabolites of *S. avermitilis* by genome analysis, Database accession No. 139:346383 CA XP-002266244 (2001).
Omura Satoshi et al, Genome sequence of an industrial microorganism *Streptomyces* . . . metabolites, PNAS, Oct. 9, 2001, vol. 98, No. 21, 12215-12220.

* cited by examiner

*Primary Examiner*—Jerry Lin
(74) *Attorney, Agent, or Firm*—Nixon & Vanderhye P.C.

(57) ABSTRACT

Novel polynucleotides derived from microorganisms belonging to actinomycetes and fragments thereof, polypeptides encoded by the polynucleotides and fragments thereof, polynucleotide arrays comprising the polynucleotides and fragments thereof, recording media in which the nucleotide sequences of the polynucleotide and fragments thereof have been recorded which are readable in a computer, and use of them.

7 Claims, 4 Drawing Sheets

POLYNUCLEOTIDES

The contents of the attached CD-R compact discs are incorporated herein be reference in the entirety. The attached discs contain an identical copy of the files listed in the following table which were created on the discs on the dates shown in the following table and have the file sizes shown in the following table:

| Name | Size | Type | Modified |
|---|---|---|---|
| seq1(1).doc | 18,273KB | Microsoft Word Doc... | 5/24/02 2:59 PM |
| seq2(2-2000).doc | 21,677KB | Microsoft Word Doc... | 5/24/02 3:03 PM |
| seq3(2001-3500).doc | 10,360KB | Microsoft Word Doc... | 5/24/02 3:30 PM |
| seq4(3501-5500).doc | 21,173KB | Microsoft Word Doc... | 5/24/02 3:28 PM |
| seq5(5501-7551).doc | 21,627KB | Microsoft Word Doc... | 5/24/02 3:25 PM |
| seq6(7552-10000).doc | 18,036KB | Microsoft Word Doc... | 5/24/02 3:21 PM |
| seq7(10001-12500).doc | 18,704KB | Microsoft Word Doc... | 5/24/02 3:16 PM |
| seq8(12501-15101).doc | 18,683KB | Microsoft Word Doc... | 5/24/02 3:12 PM |
| seq9(15102-15109).doc | 821KB | Microsoft Word Doc... | 5/24/02 3:08 PM |
| seq1(1).txt | 11,616KB | Text Document | 5/29/02 10:21 AM |
| seq2(2-2000).txt | 8,852KB | Text Document | 5/29/02 11:21 AM |
| seq3(2001-3500).txt | 7,207KB | Text Document | 5/29/02 11:22 AM |
| seq4(3501-5500).txt | 8,653KB | Text Document | 5/29/02 11:22 AM |
| seq5(5501-7551).txt | 8,884KB | Text Document | 5/29/02 11:26 AM |
| seq6(7552-10000).txt | 7,158KB | Text Document | 5/29/02 11:27 AM |
| seq7(10001-12500).txt | 7,329KB | Text Document | 5/29/02 11:28 AM |
| seq8(12501-15101).txt | 7,437KB | Text Document | 5/29/02 11:29 AM |
| seq9(15102-15109).txt | 288KB | Text Document | 5/29/02 11:29 AM |

BACKGROUND OF THE INVENTION

1. Field of the Invention

The present invention relates to novel polynucleotides derived from microorganisms belonging to actinomycetes (actinobacteria) and fragments thereof, polypeptides encoded by the polynucleotides and fragments thereof, polynucleotide arrays comprising the polynucleotides and fragments thereof, computer readable recording media in which the nucleotide sequences of the polynucleotide and fragments thereof have been recorded, and use of them as well as a method of using the polynucleotide and/or polypeptide sequence information to make comparisons.

2. Brief Description of the Background Art

Actinomycetes are used in producing various biological active substances comprising an antibiotic which is obtained from a precursor such as amino acid, nucleic acid, vitamin, saccharide, organic acid, analogues thereof and the like, and are very useful microorganisms industrially. Many mutants thereof are known.

For example, *Streptomyces avermitilies* is a Gram-positive bacterium identified as an avermectin-producing bacterium having parasiticidal activity and insecticidal activity, and avermectin is produced by mutants thereof. The avermectin is used as a parasiticide of livestock worldwide, and is used as an agent for treating and preventing human onchocerciasis in countries of tropical regions where the onchocerciasis is prevalent. The production of avermectin using *Streptomyces avermitilis* is carried out in a mutant (metabolic mutant) of which metabolic pathway and its regulation mechanism are changed. However, accumulation of basic genetic, biochemical and molecular biological data on actinomycetes is insufficient in comparison with *Escherichia coli, Bacillus subtilis*, and the like. Also, few findings have been obtained on mutated genes in biological active substance-producing mutants. Thus, there are various mechanisms, which are still unknown, of regulating the growth and metabolism of these microorganisms.

A chromosomal map by crossing of *Streptomyces avermitilis* ATCC 31267 is reported and it is known that its genome size is about 8,000 kb (*Mol. Gen. Genet.*, 252: 255-265 (1996)). Calculating on the basis of the usual gene density of bacteria, it is presumed that about 8,000 genes are present in this genome of about 8,000 kb. However, only about several ten genes mainly concerning avermectin biosynthetic genes are known in *Streptomyces avermitilis*, and the nucleotide sequences of most genes have not been clarified hitherto.

In recent years, the full nucleotide sequence of the genomes of several microorganisms, such as *Escherichia coli, Mycobacterium tuberculosis*, yeast, and the like, have been determined (*Science*, 277: 1453-62 (1997); *Nature*, 393: 537-544 (1998); *Nature*, 387: 5-105 (1997)). Based on the thus determined full nucleotide sequences, assumption of gene regions and prediction of their function by comparison with the nucleotide sequences of known genes have been carried out. Thus, the functions of a great number of genes have been presumed, without genetic, biochemical or molecular biological experiments.

In recent years, moreover, techniques for monitoring expression levels of a great number of genes simultaneously or detecting mutations, using DNA chips, DNA arrays or the like in which a partial nucleic acid fragment of a gene or a partial nucleic acid fragment in genome DNA other than a gene is fixed to a solid support, have been developed. The techniques contribute to the analysis of microorganisms, such as yeasts, *Mycobacterium tuberculosis, Mycobacterium bovis* used in BCG vaccines, and the like (*Science*, 278: 680-686 (1997); *Proc. Natl. Acad. Sci. USA*, 96; 12833-38 (1999); *Science*, 284: 1520-23 (1999)).

SUMMARY OF THE INVENTION

An object of the present invention is to provide a polynucleotide and a polypeptide derived from a microorganism of actinomycetes which are industrially useful, sequence information of the polynucleotide and the polypeptide, a method for analyzing the microorganism, an apparatus and a system for use in the analysis, and a method for breeding the microorganism.

The present invention provides a polynucleotide and an oligonucleotide derived from a microorganism belonging to actinomycetes, oligonucleotide arrays to which the polynucleotides and the oligonucleotides are fixed, a polypeptide encoded by the polynucleotide, an antibody which recognizes the polypeptide, polypeptide arrays to which the polypeptides or the antibodies are fixed, a computer readable recording medium in which the nucleotide sequences of the polynucleotide and the oligonucleotide and the amino acid sequence of the polypeptide have been recorded, and a system based on the computer using the recording medium as well as a method of using the polynucleotide and/or polypeptide sequence information to make comparisons.

DETAILED DESCRIPTION OF THE INVENTION

Figure 1:
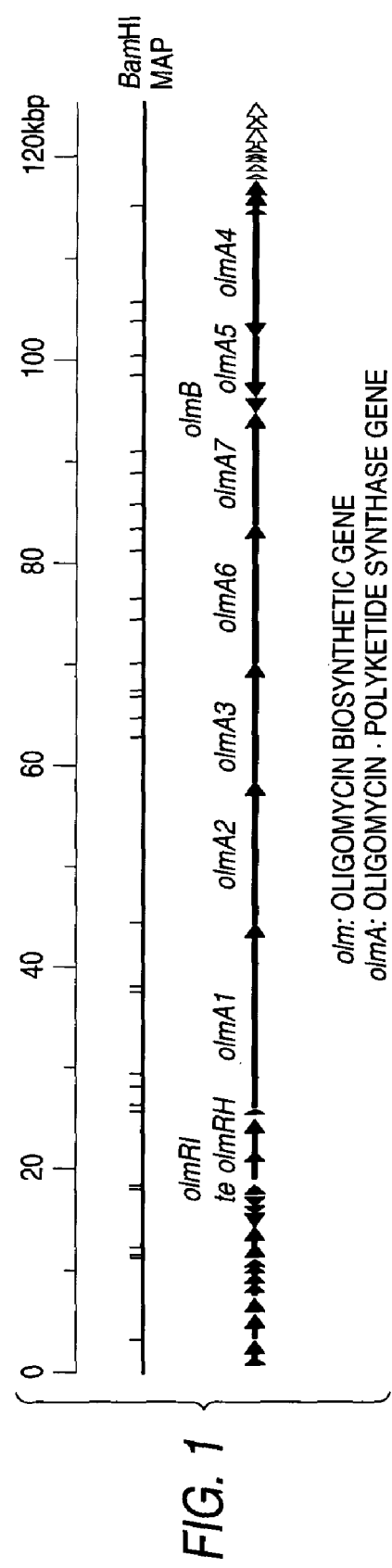
FIG. 1 is a drawing showing the construction of the gene in the region relating to the biosynthesis of oligomycin on the genome of *Streptomyces avermitilis* ATCC 31267.

This application is based on Japanese applications No. 2001-204089 filed on May 30, 2001 and No. 2001-272697 filed on Aug. 2, 2001, the entire contents of which are incorporated hereinto by reference.

From the viewpoint that the determination of the full nucleotide sequence of *Streptomyces avermitilis* would make it possible to specify gene regions which had not been previously identified, to determine the function of an unknown gene derived from the microorganism through comparison with nucleotide sequences of known genes and amino acid sequences of known genes, and to obtain a useful mutant based on the presumption of the metabolic regulatory mechanism of a useful product by the microorganism, the inventors conducted intensive studies and, as a result, found that the complete genome sequence of *Streptomyces avermitilis* can be determined by applying the whole genome shotgun method.

Specifically, the present invention relates to the following (1) to (53):

(1) A method for at least one of the following:
(A) identifying a mutation point of a gene derived from a mutant of an actinomycetes,
(B) measuring an expression amount of a gene derived from an actinomycetes,
(C) analyzing an expression profile of a gene derived from an actinomycetes,
(D) analyzing expression patterns of genes derived from an actinomycetes, or
(E) identifying a gene homologous to a gene derived from an actinomycetes,
said method comprising:
(a) producing a polynucleotide array by adhering to a solid support at least two polynucleotides selected from the group consisting of first polynucleotides comprising the nucleotide sequence represented by any one of SEQ ID NOs:1 to 7551, second polynucleotides which hybridize with the first polynucleotides under stringent conditions, and third polynucleotides comprising a sequence of 10 to 200 continuous bases of the first or second polynucleotides,
(b) incubating the polynucleotide array with at least one of a labeled polynucleotide derived from an actinomycetes, a labeled polynucleotide derived from a mutant of the actinomycetes or a labeled polynucleotide to be examined, under hybridization conditions,
(c) detecting any hybridization, and
(d) analyzing the result of the hybridization.

(2) The method according to (1), wherein the actinomycetes is a microorganism belonging to the genus *Streptomyces*, the genus *Streptosporangium*, the genus *Amycolatopsis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, or the genus *Micromonospora*.

(3) The method according to (2), wherein the microorganism belonging to the genus *Streptomyces* is selected from *Streptomyces avermitilis*.

(4) The method according to (1), wherein the labeled polynucleotide derived from an actinomycetes, the labeled polynucelotide derived from a mutant of the actinomycetes or the labeled polynucleotide to be examined is a gene relating to the biosynthesis of at least one compound selected from an amino acid, a nucleic acid, a vitamin, a saccharide, an organic acid, an antibiotic, and analogues thereof.

(5) The method according to (1), wherein the labeled polynucleotide to be examined is derived from *Escherichia coli*.

(6) A polynucleotide array, comprising:
at least two polynucleotides selected from the group consisting of first polynucleotides comprising the nucleotide sequence represented by any one of SEQ ID NOs:1 to 7551, second polynucleotides which hybridize with the first polynucleotides under stringent conditions, and third polynucleotides comprising 10 to 200 continuous bases of the first or second polynucleotides, and
a solid support adhered thereto.

(7) A polynucleotide comprising the nucleotide sequence represented by SEQ ID NOs:1 to 7551 or a polynucleotide having a homology of at least 80% with the polynucleotide.

(8) A polynucleotide comprising any one of the nucleotide sequences represented by SEQ ID NOs:2 to 7551, or a polynucleotide which hybridizes with the polynucleotide under stringent conditions.

(9) A polynucleotide encoding a polypeptide having any one of the amino acid sequences represented by SEQ ID NOs: 7552 to 15101, or a polynucleotide which hybridizes therewith under stringent conditions.

(10) A polynucleotide which is present in the 5' upstream or 3' downstream of a polynucleotide encoding a protein in a polynucleotide comprising any one of the nucleotide sequence represented by SEQ ID NOs:2 to 3431, and has an activity of regulating an expression of the polynucleotide.

(11) A polynucleotide comprising 10 to 200 continuous bases in the nucleotide sequence of the polynucleotide of any one of (7) to (10), or a polynucleotide comprising a nucleotide sequence complementary to the polynucleotide comprising 10 to 200 continuous based.

(12) A recombinant DNA comprising the polynucleotide of any one of (8) to (11).

(13) A transformant comprising the polynucleotide of any one of (8) to (11) or the recombinant DNA of (12).

(14) A method for producing a polypeptide, comprising:
culturing the transformant of (13) in a medium to produce and accumulate a polypeptide encoded by the polynucleotide of (8) or (9) in the medium, and
recovering the polypeptide from the medium.

(15) A method for producing at least one of a biological active substance comprising an antibiotic and analogues thereof, comprising:

culturing the transformant of (13) in a medium to produce and accumulate at least one of a biological active substance comprising an antibiotic and analogues thereof in the medium, and recovering the at least one of the biological substance comprising an antibiotic and analogues thereof from the medium.

(16) A polypeptide encoded by a polynucleotide comprising the nucleotide sequence selected from SEQ ID NOs:2 to 7551.

(17) A polypeptide comprising the amino acid sequence selected from SEQ ID NOs:7552 to 15101.

(18) The polypeptide according to (16) or (17), wherein at least one amino acid is deleted, replaced, inserted or added, said polypeptides having an activity which is substantially the same as that of the polypeptide without said at least one amino acid deletion, replacement, insertion or addition.

(19) A polypeptide comprising an amino acid sequence having a homology of at least 60% with the amino acid sequence of the polypeptide of (16) or (17), and having an activity which is substantially the same as that of the polypeptide.

(20) An antibody which recognizes the polypeptide of any one of (16) to (19).

(21) A polypeptide array, comprising:
at least one polypeptide or partial fragment polypeptide selected from the polypeptides of (16) to (19) and partial fragment polypeptides of the polypeptides, and a solid support adhered thereto.

(22) A polypeptide array, comprising:
at least one antibody which recognizes a polypeptide or partial fragment polypeptide selected from the polypeptides of (16) to (19) and partial fragment polypeptides of the polypeptides, and
a solid support adhered thereto.

(23) A system based on a computer for identifying a target sequence or a target structure motif derived from an actinomycetes, comprising the following:
(i) a user input device that inputs at least one nucleotide sequence information selected from SEQ ID NOs:1 to 7551, and target sequence or target structure motif information;
(ii) a data storage device for at least temporarily storing the input information;
(iii) a comparator that compares the at least one nucleotide sequence information selected from SEQ ID NOs:1 to 7551 with the target sequence or target structure motif information, recorded by the data storage device for screening and analyzing nucleotide sequence information which is coincident with or analogous to the target sequence or target structure motif information; and
(iv) an output device that shows a screening or analyzing result obtained by the comparator.

(24) A method based on a computer for identifying a target sequence or a target structure motif derived from an actinomycetes, comprising the following:
(i) inputting at least one nucleotide sequence information selected from SEQ ID NOs:1 to 7551, target sequence information or target structure motif information into a user input device;
(ii) at least temporarily storing said information;
(iii) comparing the at least one nucleotide sequence information selected from SEQ ID NOs:1 to 7551 with the target sequence or target structure motif information; and
(iv) screening and analyzing nucleotide sequence information which is coincident with or analogous to the target sequence or target structure motif information.

(25) A system based on a computer for identifying a target sequence or a target structure motif derived from an actinomycetes, comprising the following:
(i) a user input device that inputs at least one amino acid sequence information selected from SEQ ID NOs:7552 to 15101, and target sequence or target structure motif information;
(ii) a data storage device for at least temporarily storing the input information;
(iii) a comparator that compares the at least one amino acid sequence information selected from SEQ ID NOs:7552 to 15101 with the target sequence or target structure motif information, recorded by the data storage device for screening and analyzing amino acid sequence information which is coincident with or analogous to the target sequence or target structure motif information; and
(iv) an output device that shows a screening or analyzing result obtained by the comparator.

(26) A method based on a computer for identifying a target sequence or a target structure motif derived from an actinomycetes, comprising the following:
(i) inputting at least one amino acid sequence information selected from SEQ ID NOs:7552 to 15101, and target sequence information or target structure motif information into a user input device;
(ii) at least temporarily storing said information;
(iii) comparing the at least one amino acid sequence information selected from SEQ ID NOs:7552 to 15101 with the target sequence or target structure motif information; and
(iv) screening and analyzing amino acid sequence information which is coincident with or analogous to the target sequence or target structure motif information.

(27) A system based on a computer for determining a function of a polypeptide encoded by a polynucleotide having a target nucleotide sequence derived from an actinomycetes, comprising the following:
(i) a user input device that inputs at least one nucleotide sequence information selected from SEQ ID NOs:2 to 7551, function information of a polypeptide encoded by the nucleotide sequence, and target nucleotide sequence information;
(ii) a data storage device for at least temporarily storing the input information;
(iii) a comparator that compares the at least one nucleotide sequence information selected from SEQ ID NOs:2 to 7551 with the target nucleotide sequence information for determining a function of a polypeptide encoded by a polynucleotide having the target nucleotide sequence which is coincident with or analogous to the polynucleotide having at least one nucleotide sequence selected from SEQ ID NOs:2 to 7551; and
(iv) an output devices that shows a function obtained by the comparator.

(28) A method based on a computer for determining a function of a polypeptide encoded by a polypeptide encoded by a polynucleotide having a target nucleotide sequence derived from an actinomycetes, comprising the following:
(i) inputting at least one nucleotide sequence information selected from SEQ ID NOs:2 to 7551, function information of a polypeptide encoded by the nucleotide sequence, and target nucleotide sequence information;
(ii) at least temporarily storing said information;
(iii) comparing the at least one nucleotide sequence information selected from SEQ ID NOs:2 to 7551 with the target nucleotide sequence information; and
(iv) determining a function of a polypeptide encoded by a polynucleotide having the target nucleotide sequence which is coincident with or analogous to the polynucleotide having at least one nucleotide sequence selected from SEQ ID NOs:2 to 7551.

(29) A system based on a computer for determining a function of a polypeptide having a target amino acid sequence derived from an actinomycetes, comprising the following:
  (i) a user input device that inputs at least one amino acid sequence information selected from SEQ ID NOs:7552 to 15101, function information based on the amino acid sequence, and target amino acid sequence information;
  (ii) a data storing device for at least temporarily storing the input information;
  (iii) a comparator that compares the at least one amino acid sequence information selected from SEQ ID NOs:7552 to 15101 with the target amino acid sequence information for determining a function of a polypeptide having the target amino acid sequence which is coincident with or analogous to the polypeptide having at least one amino acid sequence selected from SEQ ID NOs:7552 to 15101; and
  (iv) an output device that shows a function obtained by the comparator.

(30) A method based on a computer for determining a function of a polypeptide having a target amino acid sequence derived from an actinomycetes, comprising the following:
  (i) inputting at least one amino acid sequence information selected from SEQ ID NOs:7552 to 15101, function information based on the amino acid sequence, and target amino acid sequence information;
  (ii) at least temporarily storing said information;
  (iii) comparing the at least one amino acid sequence information selected from SEQ ID NOs:7552 to 15101 with the target amino acid sequence information; and
  (iv) determining a function of a polypeptide having the target amino acid sequence which is coincident with or analogous to the polypeptide having at least one amino acid sequence selected from SEQ ID NOs:7552 to 15101.

(31) The system according to any one of (23), (25), (27) and (29), wherein an actinomycetes is a microorganism of the genus *Streptomyces*, the genus *Streptosporangium*, the genus *Amycolatopsis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, or the genus *Micromonospora*.

(32) The method according to any one of (24), (26), (28) and (30), wherein an actinomycetes is a microorganism of the genus *Streptomyces*, the genus *Streptosporangium*, the genus *Amycolatopsis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, or the genus *Micromonospora*.

(33) The system according to (31), wherein the microorganism belonging to the genus *Streptomyces* is selected from *Streptomyces avermitilis*.

(34) The method according to (32), wherein the microorganism belonging to the genus *Streptomyces* is selected from *Streptomyces avermitilis*.

(35) A recording medium or storage device which is readable by a computer in which nucleotide sequence information of SEQ ID NO:1 or function information based on the nucleotide sequence is recorded, and is usable in the system of (23) or (27) or the method of (24) or (28).

(36) A recording medium or storage device which is readable by a computer in which at least one amino acid sequence information selected from SEQ ID NOs:7552 to 15101 or function information based on the amino acid sequence is recorded, and is usable in the system of (25) or (29) or the method of (26) or (30).

(37) The recording medium or storage device according to (35) or (36), which is a computer readable recording medium selected from the group consisting of a floppy disc, a hard disc, a magnetic tape, a random access memory (RAM), a read only memory (ROM), a magneto-optic disc (MO), CD-ROM, CD-R, CD-RW, DVD-ROM, DVD-RAM and DVD-RW.

(38) A method for breeding an actinomycetes using the nucleotide sequence information represented by SEQ ID NO:1, comprising the following:
  (i) comparing a nucleotide sequence of a genome or gene of a production strain derived an actinomycetes which has been subjected to mutation breeding so as to produce at least one compound selected from an amino acid, a nucleic acid, a vitamin, a saccharide, an organic acid, an antibiotic, and analogous thereof by a fermentation method, with a corresponding nucleotide sequence in SEQ ID NO:1;
  (ii) identifying a mutation point present in the production strain based on a result obtained by (i);
  (iii) introducing the mutation point into an actinomycetes which is free of the mutation point, or deleting the mutation point from an actinomycetes having the mutation point; and
  (iv) examining productivity by the fermentation method of the compound selected in (i) of the actinomycetes obtained in (iii).

(39) The method according to (38), wherein the gene is a gene encoding an enzyme in a biosynthetic pathway or a signal transmission pathway.

(40) The method according to (38), wherein the mutation point is a mutation point relating to a useful mutation which improves or stabilizes the productivity.

(41) A method for breeding an actinomycetes using the nucleotide sequence information represented by SEQ ID NO:1, comprising:
  (i) comparing a nucleotide sequence of a genome or gene of a production strain derived an actinomycetes which has been subjected to mutation breeding so as to produce at least one compound selected from a biological active substance comprising an antibiotic and analogous thereof by a fermentation method, with a corresponding nucleotide sequence in SEQ ID NO:1;
  (ii) identifying a mutation point present in the production strain based on a result obtain by (i);
  (iii) deleting a mutation point from an actinomycetes having the mutation point; and
  (iv) examining productivity by the fermentation method of the compound selected in (i) of the actinomycetes obtained in (iii).

(42) The method according to (41), wherein the gene is a gene encoding an enzyme in a biosynthetic pathway or a signal transmission pathway.

(43) The method according to (41), wherein the mutation point is a mutation point which decreases or destabilizes the productivity.

(44) A method for breeding an actinomycetes using the nucleotide sequence information represented by SEQ ID NOs:2 to 7551, comprising the following:
  (i) identifying an isozyme relating to biosynthesis of at least one compound selected from an amino acid, a nucleic acid, a vitamin, a saccharide, an organic acid, an antibiotic, and analogous thereof, based on the nucleotide sequence information represented by SEQ ID NOs:2 to 7551;
(ii) classifying the isozyme identified in (i) into an isozyme having the same activity;
(iii) mutating all genes encoding the isozyme having the same activity simultaneously; and
(iv) examining productivity by a fermentation method of the compound selected in (i) of the actinomycetes which have been transformed with the gene obtained in (iii).
(45) A method for breeding an actinomycetes using the nucleotide sequence information represented by SEQ ID NOs:2 to 7551, comprising the following:
(i) arranging a function information of an open reading frame (ORF) represented by SEQ ID NOs:2 to 7551;
(ii) allowing the arranged ORF to correspond to an enzyme on a known biosynthesis or signal transmission pathway;
(iii) explicating an unknown biosynthesis pathway or signal transmission pathway of an actinomycetes in combination with information relating known biosynthesis pathway or signal transmission pathway of an actinomycetes;
(iv) comparing the pathway explicated in (iii) with a biosynthesis pathway of a target useful product; and
(v) transgenetically varying an actinomycetes based on the nucleotide sequence information represented by SEQ ID NOs:2 to 7551 to either strengthen a pathway which is judged to be important in the biosynthesis of the target useful product in (iv) or weaken a pathway which is judged not to be important in the biosynthesis of the target useful product in (iv).
(46) A actinomycetes, bred by the method of any one of (38) to (45).
(47) The actinomycetes according to (46), which is a microorganism belonging to the genus *Streptomyces*, the genus *Streptosporangium*, the genus *Amycolatopsis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, or the genus *Micromonospora*.
(48) The actinomycetes according to (47), wherein the microorganism belonging to the genus *Streptomyces* is selected from *Streptomyces avermoitilis*.
(49) A method for producing at least one compound selected from an amino acid, a nucleic acid, a vitamin, a saccharide, an organic acid, an antibiotic, and an analogue thereof, comprising:
culturing an actinomycetes of any one of (46) to (48) in a medium to produce and accumulate at least one compound selected from an amino acid, a nucleic acid, a vitamin, a saccharide, an organic acid, an antibiotic, and analogues thereof;
recovering the compound from the culture.
(50) The method according to (49), wherein the compound is polyketide.
(51) A method for identifying a protein relating to useful mutation based on proteome analysis, comprising the following:
(i) preparing
a protein derived from a bacterium of a production strain of an actinomycetes which has been subjected to mutation breeding by a fermentation process so as to produce at least one compound selected from an amino acid, a nucleic acid, a vitamin, a saccharide, an organic acid, an antibiotic, and analogues thereof, and a protein derived from a bacterium of a parent strain of the production strain;
(ii) separating the proteins prepared in (i) by two dimensional electrophoresis;
(iii) detecting the separated proteins, and comparing an expression amount of the protein derived from the production strain with that derived from the parent strain;
(iv) treating the protein showing different expression amounts as a result of the comparison with a peptidase to extract peptide fragments;
(v) analyzing amino acid sequences of the peptide fragments obtained in (iv); and
(vi) comparing the amino acid sequences obtained in (v) with the amino acid sequence represented by SEQ ID NOs:7552 to 15101 to identifying the protein having the amino acid sequences.
(52) The method according to (51), wherein the actinomycetes is a microorganism belonging to the genus *Streptomyces*, the genus *Streptosporangium*, the genus *Amycolatopsis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, or the genus *Micromonospora*.
(53) The method according to (52), wherein the microorganism belonging to the genus *Streptomyces* is selected from *Streptomyces avermitilis*.

The present invention will be described below in more detail, based on the determination of the full nucleotide sequence of actinomycetes.

1. Determination of Full Nucleotide Sequence of Actinomycetes

The term "actinomycetes" as used herein means a microorganism belonging to the genus *Streptomyces*, the genus *Streptosporangium*, the genus *Amycolatopsis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, or the genus *Micromonospora* as defined in Bergeys Manual of Determinative Bacteriology, 8: 599 (1974).

Examples include *Streptomyces avermitilis*, *Streptomyces griseus*, *Streptomyces hygroscopicus*, and the like.

Specific examples include *Streptomyces avenmitilis* ATCC 31267 and the like.

(1) Preparation of Genome DNA of Actinomycetes

Actinomycetes can be cultured by a conventional method. Any of a natural medium and a synthetic medium can be used, so long as it is a medium suitable for efficient culturing of the microorganism, and it contains a carbon source, a nitrogen source, an inorganic salt, and the like which can be assimilated by the microorganism.

In *Streptomyces avermitilis*, for example, TSB medium (17 g/l peptone, 3 g/l soybean peptone, 5 g/l sodium chloride, 2.5 g/l glucose, 2.5 g/l potassium secondary phosphate, pH 7.3) and the like can be used. The culturing is carried out at 25 to 35° C. overnight.

After the completion of the culture, the cells are recovered from the culture by centrifugation. The resulting cells are washed with a washing solution.

Examples of the washing solution include STE buffer (10.3% sucrose, 25 mmol/l Tris hydrochloride, 25 mmol/l ethylenediaminetetraacetic acid (hereinafter referred to as "EDTA"), pH 8.0), and the like.

In order to obtain genome DNA from the washed cells, the cells are wrapped with agarose, the cell wall of the cells is lysed using a lysozyme and a surfactant (SDS, sarcosyl, etc.), proteins are decomposed with proteinase K. Furthermore, agarose gel block comprising the genome DNA is subjected to field-inversion electrophoresis to eliminate linear plasmids. Specifically, the following method can be illustrated.

Washed cells obtained from a 5 ml culturing solution are suspended in 2.5 ml of STE buffer, and mixed with 2.5 ml of 1.5% low melting point agarose for preparing a pulse field electrophoresis sample (InCert agarose, manufactured by Takara Shuzo). The mixture is poured into a Petri dish having a 80 mm diameter, allowed to stand at room temperature for at least 30 minutes, and solidified. STE buffer (20 ml) containing lysozyme (1 to 5 mg/ml) is added thereto, and the mixture is kept at 30° C. for 6 to 20 hours to thereby digest the cell wall. The STE buffer is removed, the cells are washed with TE buffer (10 mmol/l Tris hydrochloride, 1 mmol/l EDTA, pH 8.0), 10 ml of a lysis buffer (0.5 mmol/l EDTA, pH 9.5, 1% sarcosyl) containing 1 mg/ml proteinase K is added thereto, and the mixture is gently shaken at 50° C. for 24 hours for lysis. After lysis, the buffer is removed, and the residue is washed with 20 ml of a 50 mmol/l EDTA solution of pH 8.0 several times. Additionally, 20 ml of a 50 mmol/l EDTA solution containing 1 mM PMSF of pH 8.0 is added thereto to thereby inactivate the remaining proteinase K.

Agarose gel containing genome DNA is cut out as a block of 5×5 mm, put into a sample ditch, an electrophoresis buffer is filled, and electrophoresis is carried out under pulse conditions of 3 seconds for a forward direction and 1 second for a backward direction at 120 volts overnight. After the electrophoresis, the agarose gel is taken out and washed with a 50 mmol/l EDTA solution of pH 8.0. The washed agarose gel is dissolved by incubation at 65° C. Tris neutral phenol (5 to 10 ml) is added thereto, followed by gently shaking at room temperature for 5 minutes, and then 5 to 10 ml of chloroform is further added thereto, followed by gently shaking for 5 minutes.

After shaking, centrifugation (10,000×g, 10 minutes, 20° C.) is carried out, and the aqueous phase is collected. The aqueous phase is subjected to extraction with 10 to 20 ml of phenol/chloroform twice, and then 1/10 volume of a 3 mol/l sodium acetate solution and 0.56 volume of isopropanol are added to the aqueous phase, followed by gently mixing to thereby precipitate genome DNA. The resulting genome DNA precipitate is washed with 70% ethanol, followed by air drying, and then dissolved in TE buffer to obtain a genome DNA solution.

(2) Construction of Shotgun Library

A method for produce a genome DNA library using the genome DNA of the actinomycetes prepared in the above (1) include a method described in *Molecular Cloning, A laboratory Manual*, Second Edition (1989) (hereinafter referred to as "*Molecular Cloning*, 2nd ed."). In particular, the following method can be exemplified to prepare a genome DNA library appropriately usable in determining the full nucleotide sequence by the shotgun method.

To 0.01 mg of the genome DNA of the actinomycetes prepared in the above (1), a buffer, such as TE buffer or the like, is added to give a total volume of 0.4 ml. Then, the genome DNA is cut by shearing force into fragments of 1 to 2 kb with HydroShare (manufactured by Gene Machines).

The treatment with the HydroShare is performed at an output of 6 twenty times. The resulting genome DNA fragments are passed through Size Sep 400 Span Column (Sepharose CL4B, manufactured by Amersham) to thereby remove fragments of 500 bp or less. The DNA fragments from which the fragments of 500 bp or less have been eliminated are blunt-ended using DNA blunting kit (manufactured by Takara Shuzo) or the like.

The resulting DNA eluate is treated with phenol/chloroform and then precipitated with ethanol to obtain a genome library insert.

The insert is ligated into a suitable vector, such as pUC18 HincII/BAP (manufactured by Takara Shuzo) or the like, using T4 DNA ligase (manufactured by Takara Shuzo) or the like. The ligation can be carried out by allowing a mixture to stand at 10 to 20° C. for 20 to 50 hours.

The resulting ligation product is precipitated with ethanol and dissolved in 5 to 20 µl of TE buffer. *Escherichia coli* is transformed in accordance with a conventional method using 0.5 to 2 µl of the ligation solution. Examples of the transformation method include electroporation using *Escherichia coli* DH5α. Electroporation can be carried out at 10 to 25 kV/cm.

The transformed *Escherichia coli* is spread on a suitable selection medium containing agar, for example, LB plate medium containing 10 to 100 mg/l ampicillin (LB medium (10 g/l bactotrypton, 5 g/l yeast extract, 10 g/l sodium chloride, pH 7.0) containing 1.5% of agar) when pUC18 is used as the cloning vector, and cultured therein. The transformant can be obtained as colonies formed on the plate medium. In this step, it is possible to select the transformant having the recombinant DNA containing the genome DNA as white colonies by adding X-gal (5-bromo-4-chloro-3-indolyl-β-D-galactopyranoside) and IPTG (isopropyl-β-thiogalactopyranoside) to the plate medium.

The transformant is allowed to stand for culturing in a 96-well titer plate to which 0.05 ml of the LB medium containing 0.1 mg/ml ampicillin has been added in each well. The resulting culture can be used in an experiment of (4) described below. Also, the culture solution can be stored at −80° C. by adding 0.05 ml per well of the LB medium containing 20% glycerol to the culture solution, followed by mixing, and the stored culture solution can be used at any time.

(3) Construction of Cosmid Library

The genome DNA (0.1 mg) of the actinomycetes prepared in the above (1) is partially digested with a restriction enzyme, such as MboI or the like, and then subjected to field-inversion electrophoresis using a low melting point agarose gel.

After the electrophoresis, agarose gel fractions mainly containing DNA fragments of about 40 kb are collected, and the agarose gel is dissolved at 65° C. After dissolution, phenol treatment and chloroform treatment are carried out in this order, and then the aqueous phase is collected, followed by ethanol precipitation.

The resulting DNA fragment is ligated to a cosmid vector having a cohesive end which can be ligated to the fragment. When the genome DNA is partially digested with MhoI, the partially digested product can be ligated to, for example, the BamHI site of pKU402 (*Actonomycetol*, 8: 21-25 (1994)).

The resulting ligation product is packaged using a packaging extract which can be prepared by a method described in *Molecular Cloning*, 2nd ed. and then used in transforming *Escherichia coli*. More specifically, the ligation product is packaged using, for example, a commercially available packaging extract, Ready-To-Go Lambda Packaging Kit (manufactured by Amersham) in accordance with the manufacture's instructions and then introduced into *Escherichia coli* XL-1-BlueMR (manufactured by Stratagene) or the like.

The thus transformed *Escherichia coli* is spread on an LB plate medium containing ampicillin, and cultured therein. The transformant can be obtained as colonies formed on the plate medium. The transformant is subjected to standing culture in a 96-well titer plate to which 0.05 ml of the LB medium containing 0.1 mg/ml ampicillin has been added.

The resulting culture can be employed in an experiment of (4) described below. Also, the culture solution can be stored at −80° C. by adding 0.05 ml per well of the LB medium containing 50% glycerol to the culture solution, followed by mixing, and the stored culture solution can be used at any time.

(4) Determination of Nucleotide Sequence (4-1) Preparation of Template

The full nucleotide sequence of genome DNA of actinomycetes can be determined basically according to the whole genome shotgun method (*Science,* 269: 496-512 (1995)).

The template used in the whole genome shotgun method can be prepared by PCR using the library prepared in the above (2) (*DNA Research,* 5: 1-9 (1998)).

Specifically, the template can be prepared as follows.

The clone derived from the whole genome shotgun library is inoculated by using a replicator (manufactured by GENETIX) into each well of a 96-well plate to which 0.08 ml per well of the LB medium containing 0.1 mg/ml ampicillin has been added, followed by static culturing at 37° C. overnight.

The culturing solution is diluted 40 folds with sterilized water, a 5 RI portion thereof is mixed with 5 μl of a solution containing 100 μg/ml M13 forward (GTGCTGCAAGGC-GATTAAGTTGG; SEQ ID NO:15104) and reverse primer (TCCGGCTCGTATGTTGTGTGGA; SEQ ID NO:15105), Ex Taq buffer (manufactured by Takara Shuzo), 5 mmol/l dATP, dGTP, dCTP and dTTP, and 0.25 U of TaKaRa Ex Taq (manufactured by Takara Shuzo), and amplification of inserted fragments is carried out using Biometra (manufactured by Biotron) at 96° C. for 5 minutes and a succeeding cycle of 96° C. for 15 seconds and 70° C. for 60 seconds 20 to 40 times. Also, 96-well reaction plate (manufactured by PE Biosystems) is used for the amplification.

The excessive primers and nucleotides are eliminated using a kit for purifying a PCR product, and the product is used as the template in the sequencing reaction.

A part of the nucleotide sequence can be determined using a double-stranded DNA plasmid as a template. The double-stranded DNA plasmid used as the template can be obtained by the following method. The clone derived from the whole genome shotgun library is inoculated into each well of a 96-well plate to which 1 ml per well of a TSB medium (17 g/l peptone, 3 g/l soybean peptone, 5 g/l sodium chloride, 2.5 g/l glucose, 2.5 g/l potassium secondary phosphate, pH 7.3) containing 0.1 mg/ml ampicillin has been added, followed by culturing under shaking at 30° C. overnight. The double-stranded DNA plasmid can be prepared from the culture solution using an automatic plasmid preparing machine KURABO PI-50 (manufactured by Kurabo Industries), a multiscreen (manufactured by Millipore) or the like, according to each protocol. The resulting purified double-stranded DNA plasmid is dissolved in water to give a concentration of about 0.1 mg/ml. Then, it can be used as the template in sequencing.

(4-2) Sequencing Reaction

The sequencing reaction can be carried out according to a commercially available sequence kit or the like. A specific method is exemplified below.

To 6 μl of a solution of ABI PRISM BigDye Terminator Cycle Sequencing Ready Reaction Kit (manufactured by PE Biosystems), 1 to 2 pmol of an M13 regular direction primer (M13-21) or an M13 reverse direction primer (M13REV) (*DNA Research,* 5: 1-9 (1998)) and 50 to 200 ng of the template prepared in the above (4-1) (the PCR product or plasmid) to give 10 μl of a sequencing reaction solution.

A dye terminator sequencing reaction (35 to 55 cycles) is carried out using this reaction solution and Biometra (manufactured by Biotron) or the like. The cycle parameter can be determined in accordance with a commercially available kit, for example, the manufacture's instructions attached with ABI PRISM Big Dye Terminator Cycle Sequencing Ready Reaction Kit.

The sample can be purified using a commercially available product, such as Multi Screen HV plate (manufactured by Millipore) or the like, using Sephadex G50 (manufactured by Pharmacia) according to the manufacture's instructions.

The thus purified reaction product is used for the analysis directly. The dried reaction product can be stored in the dark at −20° C. and the stored reaction product can be used at any time.

The reaction product can be analyzed using a commercially available sequencer and an analyzer according to the manufacture's instructions.

Examples of the commercially available sequencer include ABI 3700 DNA Sequencer (manufactured by PE Biosystems), Mega Bace 1000 Sequencer (manufactured by Amersham) and the like. Example of the analyzer include ABI PRISM 3700 DNA Analyzer (manufactured by PE Biosystems) and the like.

(5) Assembly

A software, such as phred (The University of Washington) or the like, can be used as base call for use in analyzing the sequence information obtained in the above (4). A software, such as Cross_Match (The University of Washington) or SPS Cross_Match (manufactured by Southwest Parallel Software) or the like, can be used to mask the vector sequence information.

For the assembly, a software, such as phrap (The University of Washington), SPS phrap (manufactured by Southwest Parallel Software) or the like, can be used.

In the above, analysis and output of the results thereof, a computer such as UNIX, Windows, Macintosh, and the like can be used. Contig obtained by the assembly can be analyzed using a graphical editor such as consed (The University of Washington) or the like. It is also possible to perform a series of the operations from the base call to the assembly in a lump using a script phredphrapi attached to the consed.

As used herein, the software will be understood to also be referred to as a comparator.

(6) Determination of Nucleotide Sequence in Gap Part

Each of the cosmids in the cosmid library constructed in the above (3) is prepared in the same manner as in the preparation of the double-stranded DNA plasmid described in the above (4-1). The nucleotide sequence at the end of the insert fragment of the cosmid is determined using a commercially available kit, such as ABI PRISM BigDye Terminator Cycle Sequencing Ready Reaction Kit (manufactured by PE Biosystems) according to the manufacture's instructions.

About 4,000 cosmid clones are sequenced at both ends of the inserted fragment to detect a nucleotide sequence in the contig derived from the shotgun sequencing obtained in (5) which is coincident with the sequence. Thus, the chain linkage between respective cosmid clones and respective contigs are clarified, and mutual alignment is carried out.

The sequence in the region which cannot be covered with the contigs (gap part) can be determined by the following method. Clones containing sequences positioned at the ends of the contigs are selected. Among these, a clone wherein only one end of the inserted fragment has been determined is selected and the sequence at the opposite end of the inserted fragment is determined. A shotgun library clone or a cosmid clone derived therefrom containing the sequences at the respective ends of the inserted fragments in the two contigs is identified and the full nucleotide sequence of the inserted fragment of the clone is determined. According to this method, the nucleotide sequence of the gap part can be determined. When no shotgun library clone or cosmid clone covering the gap part is available, primers complementary to the end sequences of the two different contigs are prepared and the DNA fragment in the gap part is amplified. Then, sequencing is performed by the primer walking method using the amplified DNA fragment as a template or by the shotgun method in which the sequence of a shotgun clone prepared from the amplified DNA fragment is determined. Thus, the nucleotide sequence of the above-described region can be determined.

In a region showing a low sequence accuracy, primers are synthesized using AUTOFINISH function and NAVIGATING function of consed (The University of Washington), and the sequence is determined by the primer walking method to improve the sequence accuracy.

Examples of the thus determined nucleotide sequence of the full genome include the full nucleotide sequence of genome of *Streptomyces avermitilis* ATCC 31267 represented by SEQ ID NO:1.

(7) Determination of Nucleotide Sequence of Microorganism Genome DNA Using the Nucleotide Sequence Represented by SEQ ID NO:1

A nucleotide sequence of a polynucleotide having a homology of 80% or more with the full nucleotide sequence of *Streptomyces avermitilis* ATCC 31267 represented by SEQ ID NO:1 as determined above can also be determined using the nucleotide sequence represented by SEQ ID NO:1, and the polynucleotide having a nucleotide sequence having a homology of 80% or more with the nucleotide sequence represented by SEQ ID NO:1 of the present invention is within the scope of the present invention. The term "polynucleotide having a nucleotide sequence having a homology of 80% or more with the nucleotide sequence represented by SEQ ID NO:1 of the present invention" is a polynucleotide in which a full nucleotide sequence of the chromosome DNA can be determined using as a primer an oligonucleotide composed of continuous 5 to 50 nucleotides in the nucleotide sequence represented by SEQ ID NO:1, for example, according to PCR using the chromosome DNA as a template.

A particularly preferred primer in determination of the full nucleotide sequence is an oligonucleotide having nucleotide sequences which are positioned at the interval of about 300 to 500 bp, and among such oligonucleotides, an oligonucleotide having a nucleotide sequence selected from DNAs encoding a protein relating to a main metabolic pathway is particularly preferred. The polynucleotide in which the full nucleotide sequence of the chromosome DNA can be determined using the oligonucleotide includes polynucleotides constituting a chromosome DNA derived from a microorganism belonging to actinomycetes. Such a polynucleotide is preferably a polynucleotide constituting chromosome DNA derived from a microorganism belonging to the genus *Streptomyces*, more preferably a polynucleotide constituting a chromosome DNA of *Streptomyces avermitilis*.

2. Identification of ORF (Open Reading Frame) and Expression Regulatory Fragment and Determination of the Function of ORF Based on the full nucleotide sequence data of the genome derived from actinomycetes determined in the above item 1, an ORF and an expression modulating fragment can be identified. Furthermore, the function of the thus determined ORF can be determined.

The ORF means a continuous region in the nucleotide sequence of mRNA which can be translated as an amino acid sequence to mature to a protein. A region of the DNA coding for the ORF of mRNA is also called ORF.

The expression modulating fragment (hereinafter referred to as "EMF") is used herein to define a series of polynucleotide fragments which modulate the expression of the ORF or another sequence ligated operatably thereto. The expression "modulate the expression of a sequence ligated operatably" is used herein to refer to changes in the expression of a sequence due to the presence of the EMF. Examples of the EMF include a promoter, an operator, an enhancer, a silencer, a ribosome-binding sequence, a transcriptional termination sequence, and the like. In actinomycetes, an EMF is usually present in an intergenic segment (a fragment positioned between two genes; about 10 to 200 nucleotides in length). Accordingly, an EMF is frequently present in an intergenic segment of 10 nucleotides or longer. It is also possible to determine or discover the presence of an EMF by using known EMF sequences as a target sequence or a target structural motif (or a target motif) using an appropriate software or comparator, such as FASTA (*Proc. Natl. Acad. Sci. USA*, 85: 2444-48 (1988)), BLAST (*J. Mol. Biol.*, 215: 403-410 (1990)) or the like. Also, it can be identified and evaluated using a known EMF-capturing vector (for example, pKK232-8; manufactured by Amersham Pharmacia Biotech).

The term "target sequence" is used herein to refer to a nucleotide sequence composed of 6 or more nucleotides, an amino acid sequence composed of 2 or more amino acids, or a nucleotide sequence encoding this amino acid sequence composed of 2 or more amino acids. A longer target sequence appears at random in a database at the lower possibility. The target sequence is preferably about 10 to 100 amino acid residues or about 30 to 300 nucleotide residues.

The term "target structural motif" or "target motif" is used herein to refer to a sequence or a combination of sequences selected optionally and reasonably. Such a motif is selected on the basis of the three-dimensional structure formed by the folding of a polypeptide by means known to one of ordinary skill in the art. Various motives are known.

Examples of the target motif of a polypeptide include, but are not limited to, an enzyme activity site, a protein-protein interaction site, a signal sequence, and the like. Examples of the target motif of a nucleic acid include a promoter sequence, a transcriptional regulatory factor binding sequence, a hair pin structure, and the like.

Examples of highly useful EMF include a high-expression promoter, an inducible-expression promoter, and the like. Such an EMF can be obtained by positionally determining the nucleotide sequence of a gene which is known or expected as achieving high expression (for example, ribosomal RNA gene: GenBank Accession No. M16175 or Z46753) or a gene showing a desired induction pattern (for example, isocitrate lyase gene induced by acetic acid: Japanese Published Unexamined Patent Application No. 56782/93) via the alignment with the full genome nucleotide sequence determined in the above item 1, and isolating the genome fragment in the upstream part (usually 200 to 500 nucleotides from the translation initiation site). It is also possible to obtain a highly useful EMF by selecting an EMF showing a high expression efficiency or a desired induction pattern from among promoters captured by the EMF-capturing vector as described above.

The ORF can be identified by extracting characteristics common to individual ORF's, constructing a general model based on these characteristics, and measuring the conformity of the subject sequence with the model. In the identification, a software, such as GeneMark (*Nuc. Acids. Res.*, 22: 4756-67 (1994): manufactured by GenePro)), GeneMark.hmm (manufactured by GenePro), GeneHacker (*Protein, Nucleic Acid and Enzyme*, 42: 3001-07 (1997)), Glimmer (*Nuc. Acids. Res.*, 26: 544-548 (1998): manufactured by The Institute of Genomic Research), or the like, can be used. In using the software, the default (initial setting) parameters are usually used, though the parameters can be optionally changed.

In the above-described comparisons, a computer, such as UNIX, Windows, Macintosh, or the like, can be used. Examples of the ORF determined by the method of the present invention include ORFs having the nucleotide sequences represented by SEQ ID NOs:2 to 7551 present in the genome of *Streptomyces avermitilis* as represented by SEQ ID NO:1. In these ORFs, polypeptides having the amino acid sequences represented by SEQ ID NOs:7552 to 15101 are encoded.

The function of an ORF can be determined by comparing the identified amino acid sequence of the ORF with known homologous sequences using a homology searching software or comparator, such as BLAST, FAST, Smith & Waterman (*Meth. Enzym.*, 164: 765 (1988)) or the like on an amino acid database, such as Swith-Prot, PIR, GenBank-nr-aa, GenPept constituted by protein-encoding domains derived from Gen-Bank database, OWL or the like.

Furthermore, by the homology searching, the identity and similarity with the amino acid sequences of known proteins can also be analyzed. With respect of the term "identity" used herein, where two polypeptides each having 10 amino acids are different in the positions of 3 amino acids, these polypeptides have an identity of 70% with each other. In case wherein one of the different 3 amino acids is analogue (for example, leucine and isoleucine), these polypeptides have a similarity of 80%.

Thus, a great number of novel genes derived from actinomycetes can be identified by determining the full nucleotide sequence of the genome derived from actinomycetes by the means of the present invention. Moreover, the function of the proteins encoded by these genes can be determined. Since actinomycetes are industrially highly useful microorganisms, many of the identified genes are industrially useful.

Moreover, the characteristics of respective microorganisms can be clarified by classifying the functions thus determined. As a result, valuable information in breeding is obtained.

Furthermore, from the ORF information derived from actinomycetes, the ORF corresponding to the microorganism is prepared and obtained according to the general method as disclosed in *Molecular Cloning*, 2nd ed. or the like. Specifically, an oligonucleotide having a nucleotide sequence adjacent to the ORF is synthesized, and the ORF can be isolated and obtained using the oligonucleotide as a primer and a chromosome DNA derived from actinomycetes as a template according to the general PCR cloning technique. Thus obtained ORF sequences include polynucleotides comprising the nucleotide sequence represented by any one of SEQ ID NOs:2 to 7551.

The ORF or primer can be prepared using a polypeptide synthesizer based on the above sequence information.

Examples of the polynucleotide of the present invention include a polynucleotide containing the nucleotide sequence of the ORF obtained in the above, and a polynucleotide which hybridizes with the polynucleotide under stringent conditions. The polynucleotide of the present invention can be a single-stranded DNA, a double-stranded DNA and a single-stranded RNA, though it is not limited thereto.

The polynucleotide which hybridizes with the polynucleotide containing the nucleotide sequence of the ORF obtained in the above under stringent conditions includes a degenerated mutant of the ORF. A degenerated mutant is a polynucleotide fragment having a nucleotide sequence which is different from the sequence of the ORF of the present invention which encodes the same amino acid sequence by degeneracy of a gene code.

Specific examples include a polynucleotide comprising the nucleotide sequence represented by any one of SEQ ID NOs:1 to 7551, and a polynucleotide which hybridizes with the polynucleotide under stringent conditions.

A polynucleotide which hybridizes under stringent conditions is a polynucleotide obtained by colony hybridization, plaque hybridization, Southern blot hybridization or the like using, as a probe, the polynucleotide having the nucleotide sequence of the ORF identified in the above. Specific examples include a polynucleotide which can be identified by carrying out hybridization at 65° C. in the presence of 0.7-1.0 M NaCl using a filter on which a polynucleotide prepared from colonies or plaques is immobilized, and then washing the filter with 0.1× to 2×SSC solution (the composition of 1×SSC contains 150 mM sodium chloride and 15 mM sodium citrate) at 65° C.

The hybridization can be carried out in accordance with known methods described in, for example, *Molecular Cloning*, 2nd ed., *Current Protocols in Molecular Biology, DNA Cloning 1: Core Techniques, A Practical Approach*, Second Edition, Oxford University (1995) or the like. Specific examples of the polynucleotide which can be hybridized include a DNA having a homology of 60% or more, preferably 80% or more, and particularly preferably 95% or more, with the nucleotide sequence represented by any one of SEQ ID NOs:2 to 7551 when calculated using default (initial setting) parameters of a homology searching software, such as BLAST, FASTA, Smith-Waterman or the like.

Also, the polynucleotide of the present invention includes a polynucleotide encoding a polypeptide comprising the amino acid sequence represented by any one of SEQ ID NOs:7552 to 15101 and a polynucleotide which hybridizes with the polynucleotide under stringent conditions.

Furthermore, the polynucleotide of the present invention includes a polynucleotide which is present in the 5' upstream or 3' downstream region of a polynucleotide comprising the nucleotide sequence of any one of SEQ ID NOs:2 to 7551 in a polynucleotide comprising the nucleotide sequence represented by SEQ ID NO:1, and has an activity of regulating an expression of a polypeptide encoded by the polynucleotide. Specific examples of the polynucleotide having an activity of regulating an expression of a polypeptide encoded by the polynucleotide includes a polynucleotide encoding the above described EMF, such as a promoter, an operator, an enhancer, a silencer, a ribosome-binding sequence, a transcriptional termination sequence, and the like.

The primer used for obtaining the ORF according to the above PCR cloning technique includes an oligonucleotide comprising a sequence which is the same as a sequence of 10 to 200 continuous nucleotides in the nucleotide sequence of the ORF and an adjacent region or an oligonucleotide comprising a sequence which is complementary to the oligonucleotide. Specific examples include an oligonucleotide comprising a sequence which is the same as a sequence of 10 to 200 continuous nucleotides of the nucleotide sequence represented by any one of SEQ ID NOs:1 to 7551, and an oligonucleotide comprising a sequence complementary to the oligonucleotide comprising a sequence of at least 10 to 20 continuous nucleotide of any one of SEQ ID NOs:1 to 7551. When the primers are used as a sense primer and an antisense primer, the above-described oligonucleotides in which melting temperature ($T_m$) and the number of nucleotides are not significantly different from each other are preferred.

The oligonucleotide of the present invention includes an oligonucleotide comprising a sequence which is the same as 10 to 200 continuous nucleotides of the nucleotide sequence represented by any one of SEQ ID NOs:1 to 7551 or an oligonucleotide comprising a sequence complementary to the oligonucleotide.

Also, analogues of these oligonucleotides (hereinafter also referred to as "analogous oligonucleotides") are also provided by the present invention and are useful in the methods described herein.

Examples of the analogous oligonucleotides include analogous oligonucleotides in which a phosphodiester bond in an oligonucleotide is converted to a phosphorothioate bond, analogous oligonucleotides in which a phosphodiester bond in an oligonucleotide is converted to an N3'-P5' phosphoamidate bond, analogous oligonucleotides in which ribose and a phosphodiester bond in an oligonucleotide is converted to a peptide nucleic acid bond, analogous oligonucleotides in which uracil in an oligonucleotide is replaced with C-5 propynyluracil, analogous oligonucleotides in which uracil in an oligonucleotide is replaced with C-5 thiazoluracil, analogous oligonucleotides in which cytosine in an oligonucleotide is replaced with C-5 propynylcytosine, analogous oligonucleotides in which cytosine in an oligonucleotide is replaced with phenoxazine-modified cytosine, analogous oligonucleotides in which ribose in an oligonucleotide is replaced with 2'-O-propylribose, analogous oligonucleotides in which ribose in an oligonucleotide is replaced with 2'-methoxyethoxyribose, and the like (Cell *Engineering*, 16: 1463 (1997)).

The above oligonucleotides and analogous oligonucleotides of the present invention can be used as probes for hybridization and antisense nucleic acids described below in addition to as primers.

Examples of a primer for the antisense nucleic acid techniques known in the art include an oligonucleotide which hybridizes the oligonucleotide of the present invention under stringent conditions and has an activity regulating expression of the polypeptide encoded by the polynucleotide, in addition to the above oligonucleotide.

3. Determination of Isozymes

Many biological active substances are produced using actinomycetes.

Examples of the biological active substances include amino acids, nucleic acids, vitamins, saccharides, organic acids, antibiotics, and the like.

Many mutants of actinomycetes which are useful in the production of useful biological active substances are obtained.

However, since the gene sequence data of the microorganism has been, to date, insufficient, useful mutants have been obtained by mutagenic techniques using a mutagen, such as nitrosoguanidine (NTG) or the like.

Although genes can be mutated randomly by the mutagenic method using the above-described mutagen, all genes encoding respective isozymes having similar properties relating to the metabolism of intermediates cannot be mutated. In the mutagenic method using a mutagen, genes are mutated randomly. Accordingly, harmful mutations worsening culture characteristics, such as delay in growth, accelerated foaming, and the like, might be imparted at a great frequency, in a random manner.

However, if gene sequence information is available, such as is provided by the present invention, it is possible to mutate all of the genes encoding target isozymes. In this case, harmful mutations may be avoided and the target mutation can be incorporated.

Namely, an accurate number and sequence information of the target isozymes in actinomycetes can be obtained based on the ORF data obtained in the above item 2. By using the sequence information, all of the target isozyme genes can be mutated into genes having the desired properties by, for example, the site-specific mutagenesis method described in *Molecular Cloning*, 2nd ed. to obtain useful mutants having elevated productivity of useful substances.

4. Clarification or Determination of Biosynthesis Pathway and Signal Transmission Pathway Attempts have been made to elucidate biosynthesis pathways and signal transmission pathways in a number of organisms, and many findings have been reported. However, there are many unknown aspects of actinomycetes since a number of genes have not been identified so far.

These unknown points can be clarified by the following method.

The functional information of ORF derived from actinomycetes as identified by the method of above item 2 is arranged. The term "arranged" means that the ORF is classified based on the biosynthesis pathway of a substance or the signal transmission pathway to which the ORF belongs using known information according to the functional information. Next, the arranged ORF sequence information is compared with enzymes on the biosynthesis pathways or signal transmission pathways of other known organisms. The resulting information is combined with known data on actinomycetes. Thus, the biosynthesis pathways and signal transmission pathways in actinomycetes, which have been unknown so far, can be determined.

As a result that these pathways which have been unknown or unclear hitherto are clarified, a useful mutant for producing a target useful substance can be efficiently obtained.

When the thus clarified pathway is judged as important in the synthesis of a useful product, a useful mutant can be obtained by selecting a mutant wherein this pathway has been strengthened. Also, when the thus clarified pathway is judged as not important in the biosynthesis of the target useful product, a useful mutant can be obtained by selecting a mutant wherein the utilization frequency of this pathway is lowered.

5. Clarification or Determination of Useful Mutation Point

Many useful mutants of actinomycetes which are suitable for the production of useful substances, such as biological active substances comprising an antibiotic, and the like, have been obtained. However, it is hardly known which mutation point is imparted to a gene to improve the productivity.

However, mutation points contained in production strains can be identified by comparing desired sequences of the genome DNA of the production strains obtained from actinomycetes by the mutagenic technique with the nucleotide sequences of the corresponding genome DNA and ORF derived from actinomycetes determined by the methods of the above items 1 and 2 and analyzing them Moreover, effective mutation points contributing to the production can be easily specified from among these mutation points on the basis of known information relating to the metabolic pathways, the metabolic regulatory mechanisms, the structure activity correlation of enzymes, and the like.

When any efficient mutation can be hardly specified based on known data, the mutation points thus identified can be introduced into a wild strain of actinomycetes or a production strain free of the mutation. Then, it is examined whether or not any positive effect can be achieved on the production.

6. Method of Breeding Industrially Advantageous Production Strain

It has been a general practice to construct production strains, which are used industrially in the fermentation production of the target useful substances, such as biological active substances comprising an antibiotic, and the like, by repeating mutagenesis and breeding based on random mutagenesis using mutagens, such as NTG or the like, and screening.

Although mutagenesis methods have largely contributed to the progress of the fermentation industry, they suffer from a serious problem of multiple, random introduction of mutations into every part of the chromosome. Since many mutations are accumulated in a single chromosome each time a strain is improved, a production strain obtained by the random mutation and selecting is generally inferior in properties (for example, showing poor growth, delayed consumption of saccharides, and poor resistance to stresses such as temperature and oxygen) to a wild type strain, which brings about troubles such as failing to establish a sufficiently elevated productivity, being frequently contaminated with miscellaneous bacteria, requiring troublesome procedures in culture maintenance, and the like, and, in its turn, elevating the production cost in practice. In addition, the improvement in the productivity is based on random mutations and thus the mechanism thereof is unclear. Therefore, it is very difficult to plan a rational breeding strategy for the subsequent improvement in the productivity.

According to the present invention, effective mutation points contributing to the production can be efficiently specified from among many mutation points accumulated in the chromosome of a production strain which has been bred from actinomycetes and, therefore, a novel breeding method of assembling these effective mutations in the actinomycetes can be established. Thus, a useful production strain can be reconstructed. It is also possible to construct a useful production strain from a wild type strain.

Specifically, a useful mutant can be constructed in the following manner.

One of the mutation points is incorporated into a wild type strain of actinomycetes. Then, it is examined whether or not a positive effect is established on the production. When a positive effect is obtained, the mutation point is saved. When no effect is obtained, the mutation point is removed. Subsequently, only a strain having the effective mutation point is used as the parent strain, and the same procedure is repeated. In general, the effectiveness of a mutation positioned upstream cannot be clearly evaluated in some cases when there is a rate-determining point in the downstream of a biosynthesis pathway. It is therefore preferred to successively evaluate mutation points upward from downstream.

By reconstituting effective mutations by the method as described above in a wild type strain or a strain which has a high growth speed or the same ability to consume saccharides as the wild type strain, it is possible to construct an industrially advantageous strain which is free of troubles in the previous methods as described above and to conduct fermentation production using such strains within a short time or at a higher temperature.

A strain having a further improved productivity of the target product can be obtained using the thus reconstructed strain as the parent strain and further breeding it using the conventional mutagenesis method, the gene amplification method, the gene replacement method using the recombinant DNA technique, the transduction method or the cell fusion method. Accordingly, the microorganism of the present invention includes, but is not limited to, a mutant, a cell fusion strain, a transformant, a transductant or a recombinant strain constructed by using recombinant DNA techniques, so long as it is a producing strain obtained via the step of accumulating at least two effective mutations in a actinomycetes in the course of breeding.

When a mutation point judged as being harmful to the growth or production is specified, on the other hand, it is examined whether or not the producing strain used at present contains the mutation point. When it has the mutation, it can be returned to the wild type gene and thus a further useful production strain can be bred.

The breeding method as described above is applicable to microorganisms, other than actinomycetes, which have industrially advantageous properties (for example, microorganisms capable of quickly utilizing less expensive carbon sources, microorganisms capable of growing at higher temperatures).

7. Production and Utilization of Polynucleotide Array (1) Production of Polynucleotide Array A polynucleotide array can be produced using the polynucleotide or oligonucleotide of the present invention obtained in the above items 1 and 2.

Examples include a polynucleotide array comprising a solid support to which at least one of a polynucleotide comprising the nucleotide sequence represented by SEQ ID NOs:2 to 7551, a polynucleotide which hybridizes with the polynucleotide under stringent conditions, and a polynucleotide comprising 10 to 200 continuous nucleotides in the nucleotide sequence of the polynucleotide is adhered; and a polynucleotide array comprising a solid support to which at least one of a polynucleotide encoding a polypeptide comprising the amino acid sequence represented by any one of SEQ ID NOs:7552 to 15101, a polynucleotide which hybridizes with the polynucleotide under stringent conditions, and a polynucleotide comprising 10 to 200 continuous bases in the nucleotide sequences of the polynucleotides is adhered.

Polynucleotide arrays of the present invention include substrates known in the art, such as a DNA chip, a DNA microarray and a DNA macroarray, and the like, and comprises a solid support and plural polynucleotides or fragments thereof which are adhered to the surface of the solid support.

Examples of the solid support include a glass plate, a nylon membrane, and the like.

The polynucleotides or fragments thereof adhered to the surface of the solid support can be adhered to the surface of the solid support using the general technique for preparing arrays. Namely, a method in which they are adhered to a chemically surface-treated solid support, for example, to which a polycation such as polylysine or the like has been adhered (*Nat. Genet.*, 21: 15-19 (1999)). The chemically surface-treated supports are commercially available and the commercially available solid product can be used as the solid support of the polynucleotide array according to the present invention.

As the polynucleotides or oligonucleotides adhered to the solid support, the polynucleotides and oligonucleotides of the present invention obtained in the above items 1 and 2 can be used.

The analysis described below can be efficiently performed by adhering the polynucleotides or oligonucleotides to the solid support at a high density, though a high fixation density is not always necessary.

Apparatus for achieving a high fixation density, such as an arrayer robot or the like, is commercially available from Takara Shuzo (GMS417 Arrayer), and the commercially available product can be used.

Also, the oligonucleotides of the present invention can be synthesized directly on the solid support by the photolithography method or the like (*Nat. Genet.*, 21: 20-24 (1999)). In this method, a linker having a protective group which can be removed by light irradiation is first adhered to a solid support, such as a slide glass or the like. Then, it is irradiated with light through a mask (a photolithograph mask) permeating light exclusively at a definite part of the adhesion part. Next, an oligonucleotide having a protective group which can be removed by light irradiation is added to the part. Thus, a ligation reaction with the nucleotide arises exclusively at the irradiated part. By repeating this procedure, oligonucleotides, each having a desired sequence, different from each other can be synthesized in respective parts. Usually, the oligonucleotides to be synthesized have a length of 10 to 30 nucleotides.

(2) Use of Polynucleotide Array

The following procedures (a) and (b) can be carried out using the polynucleotide array prepared in the above (1).

(a) Identification of Mutation Point of Actinomycetes Mutant and Analysis of Expression Amount and Expression Profile of Gene Encoded by Genome By subjecting a gene derived from a mutant of actinomycetes or an examined gene td the following steps (i) to (iv), the mutation point of the gene can be identified or the expression amount and expression profile of the gene can be analyzed:

(i) producing a polynucleotide array by the method of the above (1);
(ii) incubating polynucleotides immobilized on the polynucleotide array together with the labeled gene derived from a mutant of the actinomycetes using the polynucleotide array produced in the above (i) under hybridization conditions;
(iii) detecting the hybridization; and
(iv) analyzing the hybridization data.

The gene derived from a mutant of actinomycetes or the examined gene include a gene relating to biosynthesis of at least one selected from amino acids, nucleic acids, vitamins, saccharides, organic acids, antibiotics, and analogues thereof.

The method will be described in detail.

A single nucleotide polymorphism (SNP) in a human region of 2,300 kb has been identified using polynucleotide arrays (*Science*, 280: 1077-82 (1998)). In accordance with the method of identifying SNP and methods described in *Science*, 278: 680-686 (1997); *Proc. Natl. Acad. Sci. USA*, 96: 12833-38 (1999); *Science*, 284: 1520-23 (1999), and the like using the polynucleotide array produced in the above (1) and a nucleic acid molecule (DNA, RNA) derived from actinomycetes in the method of the hybridization, a mutation point of a useful mutant, which is useful in producing an amino acid, a nucleic acid, a vitamin, a saccharide, an organic acid, or the like can be identified and the gene expression amount and the expression profile thereof can be analyzed.

The nucleic acid molecule (DNA, RNA) derived from the actinomycetes can be obtained according to the general method described in *Molecular Cloning*, 2nd ed. or the like. Although ribosomal RNA (rRNA) is usually obtained in large excess in addition to the target mRNA, the analysis is not seriously disturbed thereby.

The resulting nucleic acid molecule derived from actinomycetes is labeled. Labeling can be carried out according to a method using a fluorescent dye, a method using a radioisotope or the like.

Specific examples include a labeling method in which psoralen-biotin is crosslinked with RNA extracted from a microorganism and, after hybridization reaction, a fluorescent dye having streptoavidin bound thereto is bound to the biotin moiety (*Nat. Biotechnol.*, 16: 45-48 (1998)); a labeling method in which a reverse transcription reaction is carried out using RNA extracted from a microorganism as a template and random primers as primers, and dUTP having a fluorescent dye (for example, Cy3, Cy5) (manufactured by Amersham Pharmacia Biotech) is incorporated into cDNA (*Proc. Natl. Acad. Sci. USA*, 96: 12833-38 (1999)); and the like.

The labeling specificity can be improved by replacing the random primers by sequences complementary to the 3'-end of ORF (*J. Bacteriol.*, 181: 6425-40 (1999)).

In the hybridization method, the hybridization and subsequent washing can be carried out by the general method (*Nat. Bioctechnol.*, 14: 1675-80 (1996), or the like).

Subsequently, the hybridization intensity is measured depending on the hybridization amount of the nucleic acid molecule used in the labeling. Thus, the mutation point can be identified and the expression amount of the gene can be calculated.

The hybridization intensity can be measured by visualizing the fluorescent signal, radioactivity, luminescence dose, and the like, using a laser confocal microscope, a CCD camera, a radiation imaging device (for example, STORM manufactured by Amersham Pharmacia Biotech), and the like, and then quantifying the thus visualized data.

A polynucleotide array on a solid support can also be analyzed and quantified using a commercially available apparatus, such as GMS418 Array Scanner (manufactured by Takara Shuzo) or the like.

The gene expression amount can be analyzed using a commercially available software (for example, ImaGene manufactured by Takara Shuzo; Array Gauge manufactured by Fuji Photo Film; ImageQuant manufactured by Amersham Pharmacia Biotech, or the like). A fluctuation in the expression amount of a specific gene can be monitored using a nucleic acid molecule obtained in the time course of culture as the nucleic acid molecule derived from actinomycetes. The culture conditions can be optimized by analyzing the fluctuation.

The expression profile of the microorganism at the total gene level (namely, which genes among a great number of genes encoded by the genome have been expressed and the expression ratio thereof) can be determined using a nucleic acid molecule having the sequences of many genes determined from the full genome sequence of the microorganism. Thus, the expression amount of the genes determined by the full genome sequence can be analyzed and, in its turn, the biological conditions of the microorganism can be recognized as the expression pattern at the full gene level.

(b) Confirmation of the Presence of Gene Homologous to Examined Gene in Actinomycetes Whether or not a gene homologous to the examined gene, which is present in an organism other than actinomycetes, is present in actinomycetes can be detected using the polynucleotide array prepared in the above (1).

This detection can be carried out by a method in which an examined gene which is present in an organism other than actinomycetes is used instead of the nucleic acid molecule derived from actinomycetes used in the above identification/analysis method of (1).

8. Recording Medium Storing Full Genome Nucleotide Sequence and ORF Data and Being Readable by a Computer and Methods for Using the Same The term "recording medium or storage device which is readable by a computer" means a recording medium or storage medium which can be directly readout and accessed with a computer. Examples include magnetic recording media, such as a floppy disk, a hard disk, a magnetic tape, and the like; optical recording media, such as CD-ROM, CD-R, CD-RW, DVD-ROM, DVD-RAM, DVD-RW, and the like; electric recording media, such as RAM, ROM, and the like; and hybrids in these categories (for example, magnetic/optical recording media, such as MO and the like).

Instruments for recording or inputting in or on the recording medium or instruments or devices for reading out the information in the recording medium can be appropriately selected, depending on the type of the recording medium and the access device utilized. Also, various data processing programs, software, comparator and formats are used for recording and utilizing the polynucleotide sequence information or the like. of the present invention in the recording medium. The information can be expressed in the form of a binary file, a text file or an ASCII file formatted with commercially available software, for example. Moreover, software for accessing the sequence information is available and known to one of ordinary skill in the art.

Examples of the information to be recorded in the above-described medium include the full genome nucleotide sequence information of actinomycetes as obtained in the above item 2, the nucleotide sequence information of ORF, the amino acid sequence information encoded by the ORF, and the functional information of polynucleotides coding for the amino acid sequences.

The recording medium or storage device which is readable by a computer according to the present invention refers to a medium in which the information of the present invention has been recorded. Examples include recording media or storage devices which are readable by a computer storing the nucleotide sequence information represented by SEQ ID NOs:1 to 7551, the amino acid sequence information represented by SEQ ID NOs:7552 to 15101, the functional information of the nucleotide sequences represented by SEQ ID NOs:1 to 7551, and the functional information of the amino acid sequences represented by SEQ ID NOs:7552 to 15101.

9. System Based on a Computer Using the Recording Medium of the Present Invention Which is Readable by a Computer The term "system based on a computer" as used herein refers a system composed of hardware device(s), software device(s), and data recording device(s) which are used for analyzing the data recorded in the recording medium of the present invention which is readable by a computer.

The hardware device(s) are, for example, composed of an input unit, a data recording unit, a central processing unit and an output unit collectively or individually.

By the software device(s), the data recorded in the recording medium of the present invention are searched or analyzed using the recorded data and the hardware device(s) as described herein. Specifically, the software device(s) contain at least one program which acts on or with the system in order to screen, analyze or compare biologically meaningful structures or information from the nucleotide sequences, amino acid sequences and the like recorded in the recording medium according to the present invention.

Examples of the software device(s) for identifying ORF and EMF domains include GeneMark (*Nuc. Acids. Res.,* 22: 4756-67 (1994)), GeneHacker (*Protein, Nucleic Acid and Enzyme,* 42: 3001-07 (1997)), Glimmer (The Institute of Genomic Research; *Nuc. Acids. Res.,* 26: 544-548 (1998)) and the like. In the process of using such a software device, the default (initial setting) parameters are usually used, although the parameters can be changed, if necessary, in a manner known to one of ordinary skill in the art.

Examples of the software device(s) for identifying a genome domain or a polypeptide domain analogous to the target sequence or the target structural motif (homology searching) include FASTA, BLAST, Smith-Waterman, GenetyxMac (manufactured by Software Development), GCG Package (manufactured by Genetic Computer Group), GenCore (manufactured by Compugen), and the like. In the process of using such a software device, the default (initial setting) parameters are usually used, although the parameters can be changed, if necessary, in a manner known to one of ordinary skill in the art.

Such a recording medium storing the full genome sequence data is useful in preparing a polynucleotide array by which the expression amount of a gene encoded by the genome DNA of actinomycetes and the expression profile at the total gene level of the microorganism, namely, which genes among many genes encoded by the genome have been expressed and the expression ratio thereof, can be determined.

The data recording device(s) provided by the present invention are, for example, memory device(s) for recording the data recorded in the recording medium of the present invention and target sequence or target structural motif data, or the like, and a memory accessing device(s) for accessing the same.

Namely, the system based on a computer according to the present invention comprises the following:

(i) a user input device that inputs the information stored in the recording medium of the present invention, and target sequence or target structure motif information;

(ii) a data storage device for at least temporarily storing the input information;

(iii) a comparator that compares the information stored in the recording medium of the present invention with the target sequence or target structure motif information, recorded by the data storing device of (ii) for screening and analyzing nucleotide sequence information which is coincident with or analogous to the target sequence or target structure motif information; and (iv) an output device that shows a screening or analyzing result obtained by the comparator.

This system is usable in the methods in items 2 to 5 as described above for searching and analyzing the ORF and EMF domains, target sequence, target structural motif, etc. of an actinomycetes, searching homologs, searching and analyzing isozymes, determining the biosynthesis pathway and the signal transmission pathway, and identifying spots which have been found in the proteome analysis. The term "homologs" as used herein includes both of orthologs and paralogs.

10. Production of Polypeptide Using ORF Derived from Actinomycetes

The polypeptide of the present invention can be produced using a polynucleotide comprising the ORF obtained in the above item 2. Specifically, the polypeptide of the present invention can be produced by expressing the polynucleotide of the present invention or a fragment thereof in a host cell, using the method described in *Molecular Cloning*, 2nd ed., *Current Protocols in Molecular Biology*, and the like, for example, according to the following method.

A DNA fragment having a suitable length containing a part encoding the polypeptide is prepared from the full length ORF sequence, if necessary.

Also, DNA in which nucleotides in a nucleotide sequence at a part encoding the polypeptide of the present invention are replaced to give a codon suitable for expression of the host cell, if necessary. The DNA is useful for efficiently producing the polypeptide of the present invention.

A recombinant vector is prepared by inserting the DNA fragment into the downstream of a promoter in a suitable expression vector.

The recombinant vector is introduced to a host cell suitable for the expression vector.

Any of bacteria, yeasts, animal cells, insect cells, plant cells, and the like can be used as the host cell so long as it can be expressed in the gene of interest.

Examples of the expression vector include those which can replicate autonomously in the above-described host cell or can be integrated into chromosome and have a promoter at such a position that the DNA encoding the polypeptide of the present invention can be transcribed.

When a prokaryote cell, such as a bacterium or the like, is used as the host cell, it is preferred that the recombinant vector containing the DNA encoding the polypeptide of the present invention can replicate autonomously in the bacterium and is a recombinant vector constituted by, at least a promoter, a ribosome binding sequence, the DNA of the present invention and a transcription termination sequence. A promoter controlling gene can also be contained therewith in operable combination.

Examples of the expression vectors include a vector plasmid which is replicable in *Streptomyces avermitilis*, such as pIJ6021 and the like; a vector plasmid which is replicable in *Escherichia coli*, such as pET3 and pET11 (manufactured by Stratagene), pBAD, pThioBis and pTrcHis (manufactured by Invitrogen), pKK223-3 and pGEX2T (manufactured by Amersham Pharmacia Biotech), and the like; and pBTrp2, pBTac1 and pBTac2 (manufactured by Boehringer Mannheim Co.), pSE280 (manufactured by Invitrogen), pGE-MEX-1 (manufactured by Promega), pQE-8 (manufactured by QIAGEN), pGEL1 (*Proc. Natl. Acad. Sci. USA*, 82: 4306 (1985)), pBluescript II SK(–) (manufactured by Stratagene), psupex, pUB110, pTP5, pC194 and pEG400 (*J. Bacteriol.*, 172: 2392 (1990)), pGEX (manufactured by Pharmacia), pET system (manufactured by Novagen), and the like.

Any promoter can be used so long as it can function in the host cell. Examples include promoters derived from *Escherichia coli*, phage and the like, such as trp promoter ($P_{trp}$), lac promoter, $P_L$ promoter, $P_R$ promoter, T7 promoter and the like. Also, artificially designed and modified promoters, such as a promoter in which two Ptrp are linked in series ($P_{trp} \times 2$), tac promoter, lacT7 promoter, letI promoter and the like, can be used.

It is preferred to use a plasmid in which the space between Shine-Dalgarno sequence which is the ribosome binding sequence and the initiation codon is adjusted to an appropriate distance (for example, 6 to 18 nucleotides).

The transcription termination sequence is not always necessary for the expression of the DNA of the present invention. However, it is preferred to arrange the transcription terminating sequence at just downstream of the structural gene. One of ordinary skill in the art will appreciate that the codons of the above-described elements may be optimized, in a known manner, depending on the host cells and environmental conditions utilized.

Examples of the host cell include microorganisms belonging to the genus *Escherichia*, the genus *Serratia*, the genus *Bacillus*, the genus *Brevibacterium*, the genus *Corynebacterium*, the genus *Microbacterium*, the genus *Pseudomonas*, the genus *Streptomyces*, the genus *Streptosporangium*, the genus *Amycolatopsis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, the genus *Micromonospora*, and the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* W3110, *Bacillus subtilis*, *Bacillus amyloliquefacines*, *Streptomyces avermitilis*, *Streptomyces griseus*, *Streptomyces hygroscopicus*, *Streptomyces coelicolor*, *Streptomyces lividans*, and the like.

When *Streptomyces avermitilis* or an analogous microorganism is used as a host, an EMF necessary for expressing the polypeptide is not always contained in the vector so long as the polynucleotide of the present invention contains an EMF. When the EMF is not contained in the polynucleotide, it is necessary to prepare the EMF separately and ligate it so as to be in operable combination. Also, when a higher expression amount or specific expression regulation is necessary, it is necessary to ligate the EMF corresponding thereto so as to put the EMF in operable combination with the polynucleotide.

With regard to the method for the introduction of the recombinant vector, any method for introducing DNA into the above-described host cells, such as a method in which a calcium ion is used (*Proc. Natl. Acad. Sci. USA*, 69: 2110 (1972)), a protoplast method (Nature), and the like, can be used. When yeast is used as the host cell, examples of the expression vector include pYES2 (manufactured by Invitrogen), YEp13 (ATCC 37115), YEp24 (ATCC 37051), YCp50 (ATCC 37419), pHS19, pHS15, and the like.

Any promoter can be used so long as it can be expressed in yeast. Examples include a promoter of a gene in the glycolytic pathway, such as hexose kinase and the like, PHO5 promoter, PGK promoter, GAP promoter, ADH promoter, gal 1 promoter, gal 10 promoter, a heat shock protein promoter, MF α1 promoter, CUP 1 promoter, and the like.

Examples of the host cell include microorganisms belonging to the genus *Saccharomyces*, the genus *Schizosaccharomyces*, the genus *Kluyveromyces*, the genus *Trichosporon*, the genus *Schwanniomyces*, the genus *Pichia*, the genus *Candida* and the like. Specific examples include *Saccharomyces cerevisiae*, *Schizosaccharomyces pombe*, *Kluyveromyces lactis*, *Trichosporon pullulans*, *Schwanniomyces alluvius*, *Candida utilis* and the like.

With regard to the method for the introduction of the recombinant vector, any method for introducing DNA into yeast, such as electroporation (*Methods. Enzymol.*, 194: 182 (1990)), a spheroplast method (*Proc. Natl. Acad. Sci. USA*, 75: 1929 (1978)), a lithium acetate method (*J. Bacteriol.*, 153:

163 (1983)), a method described in *Proc. Natl. Acad. Sci. USA*, 75: 1929 (1978) and the like, can be used.

When animal cells are used as the host cells, examples of the expression vector include pcDNA3.1, pSinRep5 and pCEP4 (manufactured by Invitorogen), pRev-Tre (manufactured by Clontech), pAxCAwt (manufactured by Takara Shuzo), pcDNAI and pcDM8 (manufactured by Funakoshi), pAGE107 (Japanese Published Unexamined Patent Application No. 22979/91; *Cytotechnology*, 3:133 (1990)), pAS3-3 (Japanese Published Unexamined Patent Application No. 227075/90), pcDM8 (*Nature*, 329: 840 (1987)), pcDNAI/Amp (manufactured by Invitrogen), pREP4 (manufactured by Invitrogen), pAGE103 (*J. Biochem.*, 101: 1307 (1987)), pAGE210, and the like.

Any promoter can be used so long as it can function in animal cells. Examples include a promoter of IE (immediate early) gene of cytomegalovirus (CMV), an early promoter of SV40, a promoter of retrovirus, a metallothionein promoter, a heat shock promoter, SRα promoter, and the like. Also, the enhancer of the IE gene of human CMV can be used together with the promoter.

Examples of the host cell include human Namalwa cell, monkey COS cell, Chinese hamster CHO cell, HST5637 (Japanese Published Unexamined Patent Application No. 299/88), and the like.

The method for introduction of the recombinant vector into animal cells is not particularly limited, so long as it is the general method for introducing DNA into animal cells, such as an electroporation method (*Cytotechnology*, 3: 133 (1990)), a calcium phosphate method (Japanese Published Unexamined Patent Application No. 227075/90), a lipofection method (*Proc. Natl. Acad. Sci. USA*, 84, 7413 (1987)), the method described in *Virology*, 52: 456 (1973), and the like.

When insect cells are used as the host cells, the polypeptide can be expressed, for example, by the method described in Bacurovirus Expression Vectors, A Laboratory Manual, W. H. Freeman and Company, New York (1992), Bio/Technology, 6: 47 (1988), or the like.

Specifically, a recombinant gene transfer vector and bacurovirus are simultaneously inserted into insect cells to obtain a recombinant virus in an insect cell culture supernatant, and then the insect cells are infected with the resulting recombinant virus to express the polypeptide.

Examples of the gene introducing vector used in the method include pBlueBac4.5, pVL1392, pVL1393 and pBlueBacIII (manufactured by Invitrogen), and the like.

Examples of the bacurovirus include *Autographa californica* nuclear polyhedrosis virus with which insects of the family Barathra are infected, and the like.

Examples of the insect cells include *Spodoptera frugiperda* oocytes Sf9 and Sf21 (Bacurovirus Expression Vectors, A Laboratory Manual, W. B. Freeman and Company, New York (1992)), *Trichoplusia ni* oocyte High 5 (manufactured by Invitrogen) and the like.

The method for simultaneously incorporating the above-described recombinant gene transfer vector and the above-described bacurovirus for the preparation of the recombinant virus include calcium phosphate method (Japanese Published Unexamined Patent Application No. 227075/90), lipofection method (*Proc. Natl. Acad. Sci. USA*, 84: 7413 (1987)) and the like.

When plant cells are used as the host cells, examples of expression vector include a Ti plasmid, a tobacco mosaic virus vector, and the like.

Any promoter can be used so long as it can be expressed in plant cells. Examples include 35S promoter of cauliflower mosaic virus (CaMV), rice actin 1 promoter, and the like.

Examples of the host cells include plant cells and the like, such as tobacco, potato, tomato, carrot, soybean, rape, alfalfa, rice, wheat, barley, and the like.

The method for introducing the recombinant vector is not particularly limited, so long as it is the general method for introducing DNA into plant cells, such as the *Agrobacterium* method (Japanese Published Unexamined Patent Application No. 140885/84, Japanese Published Unexamined Patent Application No. 70080/85, WO 94/00977), the electroporation method (Japanese Published Unexamined Patent Application No. 251887/85), the particle gun method (Japanese Patents 2606856 and 2517813), and the like.

The transformant of the present invention includes a transformant containing the polypeptide of the present invention per se rather than as a recombinant vector, that is, a transformant containing the polypeptide of the present invention which is integrated into a chromosome of the host, in addition to the transformant containing the above recombinant vector.

When expressed in yeasts, animal cells, insect cells or plant cells, a glycopolypeptide or glycosylated polypeptide can be obtained.

The polypeptide can be produced by culturing the thus obtained transformant of the present invention in a culture medium to produce and accumulate the polypeptide of the present invention or any polypeptide expressed under the control of an EMF of the present invention, and recovering the polypeptide from the culture.

Culturing of the transformant of the present invention in a culture medium is carried out according to the conventional method as used in culturing of the host.

When the transformant of the present invention is obtained using a prokaryote, such as *Escherichia coli* or the like, or a eukaryote, such as yeast or the like, as the host, the transformant is cultured.

Any of a natural medium and a synthetic medium can be used, so long as it contains a carbon source, a nitrogen source, an inorganic salt and the like which can be assimilated by the transformant and can perform culturing of the transformant efficiently.

Examples of the carbon source include those which can be assimilated by the transformant, such as carbohydrates (for example, glucose, fructose, sucrose, molasses containing them, starch, starch hydrolysate, and the like), organic acids (for example, acetic acid, propionic acid, and the like), and alcohols (for example, ethanol, propanol, and the like).

Examples of the nitrogen source include ammonia, various ammonium salts of inorganic acids or organic acids (for example, ammonium chloride, ammonium sulfate, ammonium acetate, ammonium phosphate, and the like), other nitrogen-containing compounds, peptone, meat extract, yeast extract, corn steep liquor, casein hydrolysate, soybean meal and soybean meal hydrolysate, various fermented cells and hydrolysates thereof, and the like.

Examples of the inorganic salt include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like. The culturing is carried out under aerobic conditions by shaking culture, submerged-aeration stirring culture or the like. The culturing temperature is preferably from 15 to 40° C., and the culturing time is generally from 16 hours to 7 days. The pH of the medium is preferably maintained at 3.0 to 9.0 during the culturing. The pH can be adjusted using an inorganic or organic acid, an alkali solution, urea, calcium carbonate, ammonia, or the like.

Also, antibiotics, such as ampicillin, tetracycline, and the like, can be added to the medium during the culturing, if necessary.

When a microorganism transformed with a recombinant vector containing an inducible promoter is cultured, an inducer can be added to the medium, if necessary. For example, isopropyl-β-D-thiogalactopyranoside (IPTG) or the like can be added to the medium when a microorganism transformed with a recombinant vector containing lac promoter is cultured, or indoleacrylic acid (IAA) or the like can by added thereto when a microorganism transformed with an expression vector containing trp promoter is cultured.

Examples of the medium used in culturing a transformant obtained using animal cells as the host cells include RPMI 1640 medium (*The Journal of the American Medical Association*, 199: 519 (1967)), Eagle's MEM medium (*Science*, 122: 501 (1952)), Dulbecco's modified MEM medium (*Virology*, 8: 396 (1959)), 199 Medium (*Proceeding of the Society for the Biological Medicine*, 73: 1 (1950)), the above-described media to which fetal calf serum has been added, and the like.

The culturing is carried out generally at a pH of 6 to 8 and a temperature of 30 to 40° C. in the presence of 5% $CO_2$ for 1 to 7 days.

Also, if necessary, antibiotics, such as kanamycin, penicillin, and the like, can be added to the medium during the culturing.

Examples of the medium used in culturing a transformant obtained using insect cells as the host cells include TNM-FH medium (manufactured by Pharmingen), Sf-900 II SFM (manufactured by Life Technologies), ExCell 400 and ExCell 405 (manufactured by JRH Biosciences), Grace's Insect Medium (*Nature*, 195: 788 (1962)), and the like.

The culturing is carried out generally at a pH of 6 to 7 and a temperature of 25 to 30° C. for 1 to 5 days.

Additionally, antibiotics, such as gentamicin and the like, can be added to the medium during the culturing, if necessary.

A transformant obtained by using a plant cell as the host cell can be used as the cell or after differentiating to a plant cell or organ. Examples of the medium used in the culturing of the transformant include Murashige and Skoog (MS) medium, White medium, media to which a plant hormone, such as auxin, cytokinine, or the like has been added, and the like.

The culturing is carried out generally at a pH of 5 to 9 and a temperature of 20 to 40° C. for 3 to 60 days.

Also, antibiotics, such as kanamycin, hygromycin and the like, can be added to the medium during the culturing, if necessary.

As described above, the polypeptide can be produced by culturing a transformant derived from a microorganism, animal cell or plant cell containing a recombinant vector to which a DNA encoding the polypeptide of the present invention has been inserted according to the general culturing method to produce and accumulate the polypeptide, and recovering the polypeptide from the culture.

The process of gene expression may include secretion of the encoded protein production or fusion protein expression and the like in accordance with the methods described in *Molecular Cloning*, 2nd ed., in addition to direct expression.

The method for producing the polypeptide of the present invention includes a method of intracellular expression in a host cell, a method of extracellular secretion from a host cell, or a method of production on a host cell membrane outer envelope. The method can be selected by changing the host cell employed or the structure of the polypeptide produced.

When the polypeptide of the present invention is produced in a host cell or on a host cell membrane outer envelope, the polypeptide can be positively secreted extracellularly according to, for example, the method of Paulson et al. (*J. Biol. Chem.*, 264: 17619 (1989)), the method of Lowe et al. (*Proc. Natl. Acad. Sci. USA*, 86: 8227 (1989); *Genes Develop.*, 4: 1288 (1990)), and/or the methods described in Japanese Published Unexamined Patent Application No. 336963/93, WO 94/23021, and the like.

Specifically, the polypeptide of the present invention can be positively secreted extracellularly by expressing it in the form that a signal peptide has been added to the foreground of a polypeptide containing an active site of the polypeptide of the present invention according to the recombinant DNA technique.

Furthermore, the amount produced can be increased using a gene amplification system, such as by use of a dihydrofolate reductase gene or the like according to the method described in Japanese Published Unexamined Patent Application No. 227075/90.

Moreover, the polypeptide of the present invention can be produced by a transgenic animal individual (transgenic nonhuman animal) or plant individual (transgenic plant).

When the transformant is the animal individual or plant individual, the polypeptide of the present invention can be produced by breeding or cultivating it so as to produce and accumulate the polypeptide, and recovering the polypeptide from the animal individual or plant individual.

Examples of the method for producing the polypeptide of the present invention using the animal individual include a method for producing the polypeptide of the present invention in an animal developed by inserting a gene according to methods known to those of ordinary skill in the art (*American Journal of Clinical Nutrition*, 63: 639S (1996), *American Journal of Clinical Nutrition*, 63: 627S (1996), *Bio/Technology*, 9: 830 (1991)).

In the animal individual, the polypeptide can be produced by breeding a transgenic nonhuman animal to which the DNA encoding the polypeptide of the present invention has been inserted to produce and accumulate the polypeptide in the animal, and recovering the polypeptide from the animal. Examples of the production and accumulation place in the animal include milk (Japanese Published Unexamined Patent Application No. 309192/88), egg and the like of the animal. Any promoter can be used, so long as it can be expressed in the animal. Suitable examples include an α-casein promoter, a β-casein promoter, a β-lactoglobulin promoter, a whey acidic protein promoter, and the like, which are specific for mammary glandular cells.

Examples of the method for producing the polypeptide of the present invention using the plant individual include a method for producing the polypeptide of the present invention by cultivating a transgenic plant to which the DNA encoding the protein of the present invention by a known method (*Tissue Culture*, 20 (1994), *Tissue Culture*, 21 (1994), *Trends in Biotechnology*, 15: 45 (1997)) to produce and accumulate the polypeptide in the plant, and recovering the polypeptide from the plant.

The polypeptide according to the present invention can also be obtained by translation in vitro.

The polypeptide of the present invention can be produced by a translation system in vitro. There are, for example, two in vitro translation methods which may be used, namely, a method using RNA as a template and another method using DNA as a template. The template RNA includes the whole RNA, mRNA, an in vitro transcription product, and the like. The template DNA includes a plasmid containing a transcriptional promoter and a target gene integrated therein and downstream of the initiation site, a PCR/RT-PCR product and the like. To select the most suitable system for the in vitro translation, the origin of the gene encoding the protein to be synthesized (prokaryotic cell/eucaryotic cell), the type of the template (DNA/RNA), the purpose of using the synthesized protein and the like should be considered. In vitro translation kits having various characteristics are commercially available from many companies (Boehringer Mannheim, Promega, Stratagene, or the like), and every kit can be used in producing the polypeptide according to the present invention.

Transcription/translation of a DNA nucleotide sequence cloned into a plasmid containing a T7 promoter can be carried out using an in vitro transcription/translation system *Escherichia coli* T7 S30 Extract System for Circular DNA (manufactured by Promega, catalogue No. L1130). Also, transcription/translation using, as a template, a linear prokaryotic DNA of a supercoil non-sensitive promoter, such as lacUW5, tac, λPL(con), λPL, or the like, can be carried out using an in vitro transcription/translation system *Escherichia coli* S30 Extract System for Linear Templates (manufactured by Promega, catalogue No. L1030). Examples of the linear prokaryotic DNA used as a template include a DNA fragment, a PCR-amplified DNA product, a duplicated oligonucleotide ligation, an in vitro transcriptional RNA, a prokaryotic RNA, and the like.

In addition to the production of the polypeptide according to the present invention, synthesis of a radioactive labeled protein, confirmation of the expression capability of a cloned gene, analysis of the function of transcriptional reaction or translation reaction, and the like can be carried out using this system.

The polypeptide produced by the transformant of the present invention can be isolated and purified using the general method for isolating and purifying an enzyme. For example, when the polypeptide of the present invention is expressed as a soluble product in the host cells, the cells are collected by centrifugation after cultivation, suspended in an aqueous buffer, and disrupted using an ultrasonicator, a French press, a Manton Gaulin homogenizer, a Dynomill, or the like to obtain a cell-free extract. From the supernatant obtained by centrifuging the cell-free extract, a purified product can be obtained by the general method used for isolating and purifying an enzyme, for example, solvent extraction, salting out using ammonium sulfate or the like, desalting, precipitation using an organic solvent, anion exchange chromatography using a resin, such as diethylaminoethyl (DEAE)-Sepharose, DIAION HPA-75 (manufactured by Mitsubishi Chemical) or the like, cation exchange chromatography using a resin, such as S-Sepharose FF (manufactured by Pharmacia) or the like, hydrophobic chromatography using a resin, such as butyl sepharose, phenyl sepharose or the like, gel filtration using a molecular sieve, affinity chromatography, chromatofocusing, or electrophoresis, such as isoelectronic focusing or the like, alone or in combination thereof.

When the polypeptide is expressed as an insoluble product in the host cells, the cells are collected in the same manner, disrupted and centrifuged to recover the insoluble product of the polypeptide as the precipitate fraction. Next, the insoluble product of the polypeptide is solubilized with a protein denaturing agent. The solubilized solution is diluted or dialyzed to lower the concentration of the protein denaturing agent in the solution. Thus, the normal configuration of the polypeptide is reconstituted. After the procedure, a purified product of the polypeptide can be obtained by a purification/isolation method similar to the above.

When the polypeptide of the present invention or its derivative (for example, a polypeptide formed by adding a sugar chain thereto) is secreted out of cells, the polypeptide or its derivative can be collected in the culture supernatant. Namely, the culture supernatant is obtained by treating the culture medium in a treatment similar to the above (for example, centrifugation). Then, a purified product can be obtained from the culture medium using a purification/isolation method similar to the above.

The polypeptide obtained by the above method is within the scope of the polypeptide of the present invention, and examples include a polypeptide encoded by a polynucleotide comprising the nucleotide sequence selected from SEQ ID NOs:2 to 7551, and a polypeptide comprising an amino acid sequence represented by any one of SEQ ID NOs:7552 to 15101.

Furthermore, a polypeptide comprising an amino acid sequence in which at least one amino acids is deleted, replaced, inserted or added in the amino acid sequence of the polypeptide and having substantially the same activity as that of the polypeptide is included in the scope of the present invention. The term "substantially the same activity as that of the polypeptide" means the same activity represented by the inherent function, enzyme activity or the like possessed by the polypeptide which has not been deleted, replaced, inserted or added. The polypeptide can be obtained using a method for introducing part-specific mutations described in, for example, *Molecular Cloning*, 2nd ed., *Current Protocols in Molecular Biology, Nuc. Acids. Res.*, 10: 6487 (1982), *Proc. Natl. Acad. Sci. USA*, 79: 6409 (1982), *Gene*, 34: 315 (1985), *Nuc. Acids. Res.*, 13: 4431 (1985), *Proc. Natl. Acad. Sci. USA*, 82: 488 (1985) and the like. For example, the polypeptide can be obtained by introducing mutation(s) to DNA encoding a polypeptide having the amino acid sequence represented by any one of SEQ ID NOs:7552 to 15101. The number of the amino acids which are deleted, replaced, inserted or added is not particularly limited; however, it is usually 1 to the order of tens, preferably 1 to 20, more preferably 1 to 10, and most preferably 1 to 5, amino acids.

The at least one amino acid deletion, replacement, insertion or addition in the amino acid sequence of the polypeptide of the present invention is used herein to refer to that at least one amino acid is deleted, replaced, inserted or added to at one or plural positions in the amino acid sequence. The deletion, replacement, insertion or addition may be caused in the same amino acid sequence simultaneously. Also, the amino acid residue replaced, inserted or added can be natural or non-natural. Examples of the natural amino acid residue include L-alanine, L-asparagine, L-asparatic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine, and the like.

Herein, examples of amino acid residues which are replaced with each other are shown below. The amino acid residues in the same group can be replaced with each other.

Group A:
leucine, isoleucine, norleucine, valine, norvaline, alanine, 2-aminobutanoic acid, methionine, O-methylserine, t-butylglycine, t-butylalanine, cyclohexylalanine;

Group B:
asparatic acid, glutamic acid, isoasparatic acid, isoglutamic acid, 2-aminoadipic acid, 2-aminosuberic acid;

Group C:
asparagine, glutamine;

Group D:
  lysine, arginine, ornithine, 2,4-diaminobutanoic acid, 2,3-diaminopropionic acid;

Group E:
  proline, 3-hydroxyproline, 4-hydroxyproline;

Group F:
  serine, threonine, homoserine;

Group G:
  phenylalanine, tyrosine.

Also, in order that the resulting mutant polypeptide has substantially the same activity as that of the polypeptide which has not been mutated, it is preferred that the mutant polypeptide has a homology of 60% or more, preferably 80% or more, and particularly preferably 95% or more, with the polypeptide which has not been mutated, when calculated, for example, using default (initial setting) parameters by a homology searching software, such as BLAST, FASTA, or the like.

Also, the polypeptide of the present invention can be produced by a chemical synthesis method, such as Fmoc (fluorenylmethyloxycarbonyl) method, tBoc (t-butyloxycarbonyl) method, or the like. It can also be synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

The transformant of the present invention can be used for objects other than the production of the polypeptide of the present invention.

Specifically, at least one component selected from an amino acid, a nucleic acid, a vitamin, a saccharide, an organic acid, an antibiotic, and analogues thereof can be produced by culturing the transformant containing the polynucleotide or recombinant vector of the present invention in a medium to produce and accumulate at least one component selected from amino acids, nucleic acids, vitamins, saccharides, organic acids, antibiotics, and analogues thereof, and recovering the same from the medium.

The biosynthesis pathways, decomposition pathways and regulatory mechanisms of amino acids, nucleic acids, vitamins, saccharides, organic acids, and analogues thereof used for the production of biological active substances comprising an antibiotic differ from organism to organism. Furthermore, the biosynthesis pathways, decomposition pathways and regulatory mechanisms of biological active substances comprising an antibiotic and analogues thereof differ from organism to organism. The productivity of such a physiologically active substance can be improved using these differences, specifically by introducing a heterogeneous gene relating to the biosynthesis thereof.

To produce such a physiologically active substance, the transformant according to the present invention can be cultured by the same method as employed in culturing the transformant for producing the polypeptide of the present invention as described above. Also, the physiologically active substance can be recovered from the culture medium in combination with, for example, the ion exchange resin method, the precipitation method and other known methods.

Examples of methods known to one of ordinary skill in the art include electroporation, calcium transfection, the protoplast method, the method using a phage, and the like, when the host is a bacterium; and microinjection, calcium phosphate transfection, the positively charged lipid-mediated method and the method using a virus, and the like, when the host is a eukaryote (*Molecular Cloning*, 2nd ed.; Spector et al., *Cells/a laboratory manual*, Cold Spring Harbour Laboratory Press, 1998)). Examples of the host include prokaryotes, lower eukaryotes (for example, yeasts), higher eukaryotes (for example, mammals), and cells isolated therefrom. As the state of a recombinant polynucleotide fragment present in the host cells, it can be integrated into the chromosome of the host. Alternatively, it can be integrated into a factor (for example, a plasmid) having an independent replication unit outside the chromosome. These transformants are usable in producing the polypeptides of the present invention encoded by the ORF of the genome of *Streptomyces avermitilis*, the polynucleotides of the present invention and fragments thereof. Alternatively, they can be used in producing arbitrary polypeptides under the regulation by an EMF of the present invention.

11. Production of Antibody Recognizing the Polypeptide of the Present Invention

An antibody which recognizes the polypeptide of the present invention, such as a polyclonal antibody, a monoclonal antibody, or the like, can be produced using, as an antigen, a purified product of the polypeptide of the present invention or a partial fragment polypeptide of the polypeptide or a peptide having a partial amino acid sequence of the polypeptide of the present invention.

(1) Production of Polyclonal Antibody

A polyclonal antibody can be produced using, as an antigen, a purified product of the polypeptide of the present invention, a partial fragment polypeptide of the polypeptide, or a peptide having a partial amino acid sequence of the polypeptide of the present invention, and immunizing an animal with the same.

Examples of the animal to be immunized include a rabbit, a goat, a rat, a mouse, a hamster, a chicken and the like.

A dosage of the antigen is preferably 50 to 100 μg per animal.

When the peptide is used as the antigen, it is preferably a peptide covalently bonded to a carrier protein, such as keyhole limpet haemocyanin, bovine thyroglobulin, or the like. The peptide used as the antigen can be synthesized by a peptide synthesizer.

The administration of the antigen is, for example, carried out 3 to 10 times at the intervals of 1 or 2 weeks after the first administration. On the 3rd to 7th day after each administration, a blood sample is collected from the venous plexus of the eyeground, and it is confirmed that the serum reacts with the antigen by the enzyme immunoassay (*Enzyme-linked Immunosorbent Assay* (*ELISA*), Igaku Shoin (1976); *Antibodies—A Laboratory Manual*, Cold Spring Harbor Laboratory (1988)) or the like.

Serum is obtained from the immunized non-human mammal with a sufficient antibody titer against the antigen used for the immunization, and the serum is isolated and purified to obtain a polyclonal antibody.

Examples of the method for the isolation and purification include centrifugation, salting out by 40-50% saturated ammonium sulfate, caprylic acid precipitation (*Antibodies, A Laboratory manual*, Cold Spring Harbor Laboratory (1988)), or chromatography using a DEAE-Sepharose column, an anion exchange column, a protein A- or G-column, a gel filtration column, and the like, alone or in combination thereof, by methods known to those of ordinary skill in the art.

(2) Production of Monoclonal Antibody (a) Preparation of Antibody-Producing Cell A rat having a serum showing an enough antibody titer against a partial fragment polypeptide of the polypeptide of the present invention used for immunization is used as a supply source of an antibody-producing cell.

On the 3rd to 7th day after the antigen substance is finally administered the rat showing the antibody titer, the spleen is excised.

The spleen is cut to pieces in MEM medium (manufactured by Nissui Pharmaceutical), loosened using a pair of forceps, followed by centrifugation at 1,200 rpm for 5 minutes, and the resulting supernatant is discarded.

The spleen in the precipitated fraction is treated with a Tris-ammonium chloride buffer (pH 7.65) for 1 to 2 minutes to eliminate erythrocytes and washed three times with MEM medium, and the resulting spleen cells are used as antibody-producing cells.

(b) Preparation of Myeloma Cells

As myeloma cells, an established cell line obtained from mouse or rat is used. Examples of useful cell lines include those derived from a mouse, such as P3-X63Ag8-U1 (hereinafter referred to as "P3-U1") (*Curr. Topics in Microbiol. Immunol.*, 81: 1 (1978); *Europ. J. Immunol.*, 6: 511 (1976)); SP2/O-Ag14 (SP-2) (*Nature*, 276: 269 (1978)): P3-X63-Ag8653 (653) (*J. Immunol.*, 123: 1548 (1979)); P3-X63-Ag8 (X63) cell line (*Nature*, 256: 495 (1975)), and the like, which are 8-azaguanine-resistant mouse (BALB/c) myeloma cell lines. These cell lines are subcultured in 8-azaguanine medium (medium in which, to a medium obtained by adding 1.5 mmol/l glutamine, $5 \times 10^{-5}$ mol/l 2-mercaptoethanol, 10 μg/ml gentamicin and 10% fetal calf serum (FCS) (manufactured by CSL) to RPMI-1640 medium (hereinafter referred to as the "normal medium"), 8-azaguanine is further added at 15 μg/ml) and cultured in the normal medium 3 or 4 days before cell fusion, and $2 \times 10^7$ or more of the cells are used for the fusion.

(c) Production of Hybridoma

The antibody-producing cells obtained in (a) and the myeloma cells obtained in (b) are washed with MEM medium or PBS (disodium hydrogen phosphate: 1.83 g, sodium dihydrogen phosphate: 0.21 g, sodium chloride: 7.65 g, distilled water: 1 liter, pH: 7.2) and mixed to give a ratio of antibody-producing cells:myeloma cells=5:1 to 10:1, followed by centrifugation at 1,200 rpm for 5 minutes, and the supernatant is discarded.

The cells in the resulting precipitated fraction were thoroughly loosened, 0.2 to 1 ml of a mixed solution of 2 g of polyethylene glycol-1000 (PEG-1000), 2 ml of MEM medium and 0.7 ml of dimethylsulfoxide (DMSO) per $10^8$ antibody-producing cells is added to the cells under stirring at 37° C., and then 1 to 2 ml of MEM medium is further added thereto several times at 1 to 2 minute intervals.

After the addition, MEM medium is added to give a total amount of 50 ml. The resulting prepared solution is centrifuged at 900 rpm for 5 minutes, and then the supernatant is discarded. The cells in the resulting precipitated fraction were gently loosened and then gently suspended in 100 ml of HAT medium (the normal medium to which $10^{-4}$ mol/l hypoxanthine, $1.5 \times 10^{-5}$ mol/l thymidine and $4 \times 10^{-7}$ mol/l aminopterin have been added) by repeated drawing up into and discharging from a measuring pipette.

The suspension is poured into a 96 well culture plate at 100 μl/well and cultured at 37° C. for 7 to 14 days in a 5% $CO_2$ incubator.

After the culturing, a part of the culture supernatant is recovered, and a hybridoma which specifically reacts with a partial fragment polypeptide of the polypeptide of the present invention is selected according to the enzyme immunoassay described in *Antibodies, A Laboratory manual*, Cold Spring Harbor Laboratory, Chapter 14 (1998) and the like.

A specific example of the enzyme immunoassay is described below.

The partial fragment polypeptide of the polypeptide of the present invention used as the antigen in the immunization is spread on a suitable plate, is allowed to react with a hybridoma culturing supernatant or a purified antibody obtained in (d) described below as a first antibody, and is further allowed to react with an anti-rat or anti-mouse immunoglobulin antibody labeled with an enzyme, a chemical luminous substance, a radioactive substance or the like as a second antibody for reaction suitable for the labeled substance. A hybridoma which specifically reacts with the polypeptide of the present invention is selected as a hybridoma capable of producing a monoclonal antibody of the present invention.

Cloning is repeated using the hybridoma twice by limiting dilution analysis (HT medium (a medium in which aminopterin has been removed from HAT medium) is firstly used, and the normal medium is secondly used), and a hybridoma which is stable and contains a sufficient amount of antibody titer is selected as a hybridoma capable of producing a monoclonal antibody of the present invention.

(d) Production of Monoclonal Antibody

The monoclonal antibody-producing hybridoma cells obtained in (c) are injected intraperitoneally into 8- to 10-week-old mice or nude mice treated with pristane (intraperitoneal administration of 0.5 ml of 2,6,10,14-tetramethylpentadecane (pristane), followed by 2 weeks of feeding) at $5 \times 10^6$ to $20 \times 10^6$ cells/animal. The hybridoma causes ascites tumor in 10 to 21 days.

The ascitic fluid is collected from the mice or nude mice, and centrifuged to remove solid contents at 3000 rpm for 5 minutes.

A monoclonal antibody can be purified and isolated from the resulting supernatant according to the method similar to that used in the polyclonal antibody.

The subclass of the antibody can be determined using a mouse monoclonal antibody typing kit or a rat monoclonal antibody typing kit. The polypeptide amount can be determined by the Lowry method or by calculation based on the absorbance at 280 nm.

The antibody obtained in the above is within the scope of the antibody of the present invention.

The antibody can be used for the general assay using an antibody, such as a radioactive material labeled immunoassay (RIA), competitive binding assay, an immunotissue chemical staining method (ABC method, CSA method, etc.), immunoprecipitation, Western blotting, ELISA assay, and the like (An introduction to *Radioimmunoassay and Related Techniques*, Elsevier Science (1986); *Techniques in Immunocytochemistry*, Academic Press, Vol. 1 (1982), Vol. 2 (1983) & Vol. 3 (1985); *Practice and Theory of Enzyme Immunoassays*, Elsevier Science (1985); *Enzyme-linked Immunosorbent Assay (ELISA)*, Igaku Shoin (1976); *Antibodies–A Laboratory Manual*, Cold Spring Harbor laboratory (1988); *Monoclonal Antibody Experiment Manual*, Kodansha Scientific (1987); *Second Series Biochemical Experiment Course*, Vol. 5, Immunobiochemistry Research Method, Tokyo Kagaku Dojin (1986)).

The antibody of the present invention can be used as it is or after being labeled with a label.

Examples of the label include radioisotope, an affinity label (e.g., biotin, avidin, or the like), an enzyme label (e.g., horseradish peroxidase, alkaline phosphatase, or the like), a fluorescence label (e.g., FITC, rhodamine, or the like), a label using a rhodamine atom, (*J. Histochem. Cytochem.*, 18: 315 (1970); *Meth. Enzym.*, 62: 308 (1979); *Immunol.*, 109: 129 (1972); *J. Immunol., Meth.*, 13: 215 (1979)), and the like.

Expression of the polypeptide of the present invention, fluctuation of the expression, the presence or absence of structural change of the polypeptide, and the presence or absence in an organism other than actinomycetes of a polypeptide corresponding to the polypeptide can be analyzed using the antibody or the labeled antibody by the above assay, or a polypeptide array or proteome analysis described below.

Furthermore, the polypeptide recognized by the antibody can be purified by immunoaffinity chromatography using the antibody of the present invention.

12. Production and Use of Polypeptide Array (1) Production of Polypeptide Array

A polypeptide array can be produced using the polypeptide of the present invention obtained in the above item 10 or the antibody of the present invention obtained in the above item 11.

The polypeptide array of the present invention includes protein chips, and comprises a solid support and the polypeptide or antibody of the present invention adhered to the surface of the solid support.

Examples of the solid support include plastic such as polycarbonate or the like; an acrylic resin, such as polyacrylamide or the like; complex carbohydrates, such as agarose, sepharose, or the like; silica; a silica-based material, carbon, a metal, inorganic glass, latex beads, and the like.

The polypeptides or antibodies according to the present invention can be adhered to the surface of the solid support according to the method described in *Biotechniques*, 27: 1258-61 (1999); *Molecular Medicine Today*, 5: 326-7 (1999); *Handbook of Experimental Immunology*, 4th edition, Blackwell Scientific Publications, Chapter 10 (1986); *Meth. Enzym.*, 34 (1974); *Advances in Experimental Medicine and Biology*, 42 (1974); U.S. Pat. No. 4,681,870; U.S. Pat. No. 4,282,287; U.S. Pat. No. 4,762,881, or the like.

The analysis described herein can be efficiently performed by adhering the polypeptide or antibody of the present invention to the solid support at a high density, though a high fixation density is not always necessary.

(2) Use of Polypeptide Array

A polypeptide or a compound capable of binding to and interacting with the polypeptides of the present invention adhered to the array can be identified using the polypeptide array to which the polypeptides of the present invention have been adhered thereto as described in the above (1).

Specifically, a polypeptide or a compound capable of binding to and interacting with the polypeptides of the present invention can be identified by subjecting the polypeptides of the present invention to the following steps (i) to (iv):

(i) preparing a polypeptide array having the polypeptide of the present invention adhered thereto by the method of the above (1);
(ii) incubating the polypeptide immobilized on the polypeptide array together with at least one of a second polypeptide or compound;
(iii) detecting any complex formed between the at least one of a second polypeptide or compound and the polypeptide immobilized on the array using, for example, a label bound to the at least one of a second polypeptide or compound, or a secondary label which specifically binds to the complex or to a component of the complex after unbound material has been removed; and
(iv) analyzing the detection data.

Specific examples of the polypeptide array to which the polypeptide of the present invention has been adhered include a polypeptide array containing a solid support to which at least one of a polypeptide containing an amino acid sequence selected from SEQ ID NOs:7552 to 15101, a polypeptide containing an amino acid sequence in which at least one amino acids is deleted, replaced, inserted or added in the amino acid sequence of the polypeptide and having substantially the same activity as that of the polypeptide, a polypeptide containing an amino acid sequence having a homology of 60% or more with the amino acid sequences of the polypeptide and having substantially the same activity as that of the polypeptides, a partial fragment polypeptide, and a peptide comprising an amino acid sequence of a part of a polypeptide.

The amount of production of a polypeptide derived from actinomycetes can be analyzed using a polypeptide array to which the antibody of the present invention has been adhered in the above (1).

Specifically, the expression amount of a gene derived from a mutant of actinomycetes can be analyzed by subjecting the gene to the following steps (i) to (iv);

(i) preparing a polypeptide array by the method of the above (1);
(ii) incubating the polypeptide array (the first antibody) together with a polypeptide derived from a mutant of actinomycetes;
(iii) detecting the polypeptide bound to the polypeptide immobilized on the array using a labeled second antibody of the present invention; and
(iv) analyzing the detection data.

Specific examples of the polypeptide array to which the antibody of the present invention is adhered include a polypeptide array comprising a solid support to which at least one of an antibody which recognizes a polypeptide comprising an amino acid sequence selected from SEQ ID NOs:7552 to 15101, a polypeptide comprising an amino acid sequence in which at least one amino acids is deleted, replaced, inserted or added in the amino acid sequence of the polypeptide and having substantially the same activity as that of the polypeptide, a polypeptide comprising an amino acid sequence having a homology of 60% or more with the amino acid sequences of the polypeptide and having substantially the same activity as that of the polypeptides, a partial fragment polypeptide, or a peptide comprising an amino acid sequence of a part of a polypeptide.

A fluctuation in an expression amount of a specific polypeptide can be monitored using a polypeptide obtained in the time course of culture as the polypeptide derived from actinomycetes. The culturing conditions can be optimized by analyzing the fluctuation.

When a polypeptide derived from a mutant of actinomycetes is used, a mutated polypeptide can be detected.

13. Identification of Useful Mutation in Mutant by Proteome Analysis

Usually, the proteome is used herein to refer to a method wherein a polypeptide is separated by two-dimensional electrophoresis and the separated polypeptide is digested with an enzyme, followed by identification of the polypeptide using a mass spectrometer (MS) and searching a database.

The two dimensional electrophoresis means an electrophoretic method which is performed by combining two electrophoretic procedures having different principles. For example, polypeptides are separated depending on molecular weight in the primary electrophoresis. Next, the gel is rotated by 900 or 1800 and the secondary electrophoresis is carried out depending on isoelectric point. Thus, various separation patterns can be achieved (JIS K 3600 2474).

In searching the database, the amino acid sequence information of the polypeptides of the present invention and the recording medium of the present invention provide for in the above items 2 and 8 can be used.

The proteome analysis of an actinomycetes and its mutant makes it possible to identify a polypeptide showing a fluctuation therebetween.

The proteome analysis of a wild type strain of actinomycetes and a production strain showing an improved productivity of a target product makes it possible to efficiently identify a mutation protein which is useful in breeding for improving the productivity of a target product or a protein of which expression amount is fluctuated.

Specifically, a wild type strain of actinomycetes and a avermectin-producing strain thereof are each subjected to the proteome analysis. Then, a spot increased in the avermectin-producing strain, compared with the wild type strain, is found and a database is searched so that a polypeptide showing an increase in yield in accordance with an increase in the lysine productivity can be identified.

As a result that a protein having a high expression level is identified by proteome analysis using the nucleotide sequence information and the amino acid sequence information, of the genome of the actinomycetes of the present invention, and a recording medium storing the sequences, the nucleotide sequence of the gene encoding this protein and the nucleotide sequence in the upstream thereof can be searched at the same time, and thus, a nucleotide sequence having a high expression promoter can be efficiently selected.

In the proteome analysis, a spot on the two-dimensional electrophoresis gel showing a fluctuation is sometimes derived from a modified protein. However, the modified protein can be efficiently identified using the recording medium storing the nucleotide sequence information, the amino acid sequence information, of the genome of actinomycetes, and the recording medium storing the sequences, according to the present invention.

Moreover, a useful mutation point in a useful mutant can be easily specified by searching a nucleotide sequence (nucleotide sequence of promoters, ORF, or the like) relating to the thus identified protein using a recording medium storing the nucleotide sequence information and the amino acid sequence information, of the genome of actinomycetes of the present invention, and a recording medium storing the sequences and using a primer designed on the basis of the detected nucleotide sequence. As a result that the useful mutation point is specified, an industrially useful mutant having the useful mutation or other useful mutation derived therefrom can be easily bred.

The present invention will be explained in detail below based on Examples. However, the present invention is not limited thereto.

EXAMPLE 1

Determination of Full Nucleotide Sequence of the Genome of *Streptomyces avermitilis*:

The full nucleotide sequence of the genome of *Streptomyces avermitilis* was determined based on the whole genome shotgun method (*Science*, 269: 496-512 (1995)). In this method, a genomic library was prepared, the terminal sequences were determined at random, and the sequences were ligated on a computer to cover the full genome. Specifically, Specifically, the following procedure was carried out.

(1) Preparation of Genome DNA of Determination of *Streptomyces avermitilis* ATCC 31267

*Streptomyces avermitilis* ATCC 31267 was cultured at 30° C. overnight in 5 ml of a TSB medium (17 g/l peptone, 3 g/l soybean peptone, 5 g/l sodium chloride, 2.5 g/l glucose, 2.5 g/l potassium secondary phosphate, pH 7.3), and the cells were recovered by centrifugation. The cells were washed with STE buffer (10.3% sucrose, 25 mmol/l Tris-HCl, 25 mmol/l EDTA, pH 8.0), mixed with 2.5 ml of a low melting point agarose for 1.5% pulse field electrophoresis sample preparation use (InCert agarose, manufactured by Takara Shuzo), poured into a Petri dish of 80 mm in diameter and then allowed to stand at room temperature for 30 minutes or more for solidification.

To the Petri dish, 20 ml of the STE buffer containing 1 to 5 mg/ml lysozyme was added, and incubated at 30° C. for 6 to 20 hours to digest the cell walls. The STE buffer was discarded, and the dish was washed with TE buffer (10 mmol/l Tris-HCl, 1 mmol/l EDTA, pH 8.0), supplemented with 10 ml of a lysis buffer (0.5 mol/l EDTA, pH 9.5, 1% sarcosyl) containing 1 mg/ml proteinase K, followed gently shaking at 50° C. for 24 hours. After the shaking, the buffer was removed and the dish was washed several times with 20 ml of a 50 mmol/l EDTA solution of pH 8.0. The remaining proteinase K was inactivated by further adding a 50 mmol/l EDTA solution of pH 8.0 containing 1 mM PMSF.

Thus treated genome DNA-containing agarose gel was cut out as a block of 5×5 mm, and put into a sample ditch of 1% agarose gel (45 mmol/l Tris-borate, 1 mmol/l EDTA, 0.1 mmol/l thiourea, pH 8.3), and the gel was filled with an electrophoresis buffer to carry out electrophoresis under pulse conditions of 3 seconds for a forward direction and 1 second for a backward direction at 120 volts overnight.

After the electrophoresis, an agarose block was cut out and washed with a 50 mmol/l EDTA solution of pH 8.0. The washed agarose block was dissolved by incubation at 65° C., Tris neutral phenol (5 to 10 ml) was added thereto, followed by gently shaking at room temperature for 5 minutes, and then 5 to 10 ml of chloroform is further added thereto, followed by gently shaking for 5 minutes.

After the shaking, centrifugation (10,000×g, 10 minutes, 20° C.) was carried out, and the aqueous phase was collected. The aqueous phase was subjected to extraction with 10 to 20 ml of phenol/chloroform twice, and then ¹⁄₁₀ volume of a 3 mol/l sodium acetate solution and 0.56 volume of isopropanol were added to the aqueous phase, followed by gently mixing to thereby precipitate genome DNA. The resulting genome DNA precipitate is washed with 70% ethanol, followed by air drying, and then dissolved in TE buffer to obtain a genome DNA solution.

The thus formed genome DNA precipitate was washed with 70% ethanol, air-dried and then dissolved in TE buffer to obtain a genome DNA solution.

(2) Construction of Shotgun Library

A buffer such as TE buffer was added to 0.1 mg of the actinomycetes genome DNA prepared in the above to give a total volume of 0.4 ml. Then, the genome DNA was cut by shearing force into fragments of 1 to 2 kb with HydroShare (manufactured by Gene Machines) at an output of 6 twenty times.

The resulting genome DNA fragments were passed through Size Sep 400 Span Column (Sepharose CL4B, manufactured by Amersham) to thereby eliminate fragments of 500 bp or less.

The DNA fragments from which the fragments of 500 bp or less had been eliminated were blunt-ended using DNA blunting kit (manufactured by Takara Shuzo).

The blunt-ended DNA fragments were recovered by subjecting to phenol/chloroform treatment and then to ethanol precipitation and used as a genome library insert.

The insert was ligated by allowing it to stand at 10 to 20° C. for 24 hours in pUC118 HincII/BAP (manufactured by Takara Shuzo) using T4 DNA ligase (manufactured by Takara Shuzo).

The thus obtained ligation reaction product was precipitated with ethanol and dissolved in 5 to 20 μl of TE buffer.

*Escherichia coli* Electro-Cells DH5α (manufactured by Takara Shuzo) was transformed by electroporation using 0.5 μl of the ligation solution.

The transformed *Escherichia coli* was cultured by spreading it on LB plate agar medium (LB medium (10 g/l Bactotripton, 5 g/l yeast extract, 10 g/l sodium chloride, pH 7.0) containing 1.5% of agar) containing 100 mg/l ampicillin and 0.4 mg/l X-gal (5-bromo-4-chloro-3-indoyl-β-D-galactopyranoside). Also, a transformant comprising a recombinant DNA containing the genome DNA was selected as a white colony.

The white colony transformant was statically cultured at 37° C. overnight in a 96 well titer plate to which LB medium containing 0.1 mg/ml ampicillin had been added at 0.05 ml/well. After the culturing, 50% glycerol was added at 0.05 ml/well to the culture medium, mixed and stored at −80° C.

(3) Construction of Cosmid Library

About 0.1 mg of the genome DNA of *Streptomyces avermitilis* ATCC 31267 was partially digested with a restriction enzyme MboI and subjected to field-inversion electrophoresis (0.3 second in forward direction, 0.1 second in backward direction) using low melting point agarose gel.

After the electrophoresis, agarose gel fractions mainly comprising DNA fragments of about 40 kb were collected, and the agarose gel was dissolved at 65° C. The dissolved solution was subjected to phenol treatment and chloroform treatment in this order, and then the aqueous phase was separated and the DNA was precipitated with ethanol.

The thus obtained DNA fragments were mixed with BamHI-digested pKU402 (*Actonomycetol.*, 8: 21-25 (1994)), adjusted to a concentration of 0.3 mg/ml and then ligated using T4 DNA ligase (manufactured by Takara Shuzo).

The thus obtained ligation product was subjected to packaging using a commercially available packaging extract, Ready-To-Go Lambda Packaging Kit (manufactured by Amersham), in accordance with the manufacture's instructions and then introduced into *Escherichia coli* XL-1-BlueMR (manufactured by Stratagene).

The transformed *Escherichia coli* was spread on an LB plate medium containing ampicillin, followed by culturing at 30° C. overnight.

The transformant was statically cultured in a 96-well titer plate supplemented with 0.05 ml/well of LB medium containing 0.1 mg/ml ampicillin, and then 50% glycerol was added to the culture medium at 0.05 ml, mixed and stored at −80° C.

(4) Determination of Nucleotide Sequence (4-1) Preparation of Template

The full nucleotide sequence of *Streptomyces avermitilis* ATCC 31267 genome was determined based on the whole genome shotgun method. The template used in this method was prepared using PCR method from the library prepared in the above item (2).

Specifically, the clones derived from the whole genome shotgun library were inoculated using a replicator (manufactured by GENETIX) into a 96 well titer plate in which LB medium containing 0.1 mg/ml ampicillin had been dispensed at 0.08 ml/well, followed by static culture at 30° C. overnight.

The culture medium was diluted 40 times with sterile water, a 5 μl portion thereof was mixed with 5 μl of a solution containing 100 μg/ml M13 forward (5'-GTGCTGCAAGGC-GATTAAGTTGG-3'; SEQ ID NO:15104) and reverse (5'-TCCGGCTCGTATGTTGTGTGGA-3'; SEQ ID NO:15105) primers, Ex Taq buffer (manufactured by Takara Shuzo), 5 nmol/l DATP, dGTP, dCTP and dTTP, and 0.25 U of TakaRa Ex Taq (manufactured by Takara Shuzo), and amplification of inserted fragments was carried out using Biometra (manufactured by Biotron) at 96° C. for 5 minutes and a succeeding cycle of 96° C. for 15 seconds and 70° C. for 60 seconds 20 to 40 times.

The excessive primers and nucleotides were eliminated using a kit for purifying a PCR product (manufactured by Amersham Pharmacia Biotech), and the product was used as the sequencing reaction template.

Also, the nucleotide sequence was determined using a double-stranded DNA plasmid as the template. The double-stranded DNA plasmid as the template was obtained by the following method. The clones derived from the whole genome shotgun library were inoculated into respective wells of a 96 well titer plate in which TSB medium (17 g/l peptone, 3 g/l soybean peptone, 5 g/l sodium chloride, 2.5 g/l glucose, 2.5 g/l potassium secondary phosphate, pH 7.3) containing 0.05 mg/ml ampicillin had been dispensed at 1 ml/well, followed by static culture at 30° C. overnight.

The double-stranded DNA plasmid was prepared from the thus obtained culture medium using a plasmid automatic preparation machine HURABO PI-50 (manufactured by KURABO) or MultiScreen (manufactured by Millipore), in accordance with the manufacture's instructions of KURABO or Millipore. The thus obtained purified double-stranded DNA plasmid was dissolved in water to give a concentration of about 0.1 mg/ml and used as the sequencing template.

(4-2) Sequencing Reaction

With 6 μl of ABI PRISM BigDye Terminator Cycle Sequencing Ready Reaction Kit (manufactured by PE Biosystems) solution, M13 forward (M13-21) primer or M13 reverse (M13 REV) primer (*DNA Research*, 5: 1-9 (1998)) and the primer (PCR product or plasmid) obtained in the item (4-1) were mixed to thereby obtain 10 μl of a sequence reaction solution. Amounts of the primer and template were 1.6 pmole and 50 to 200 ng, respectively.

Using the reaction solution, 45 cycles of dye terminator sequence reaction was carried out by GeneAmp PCR System 9700 (manufactured by PE Biosystems). The cycle parameters were used in accordance with the manufacture's instructions of ABI PRISM BigDye Terminator Cycle Sequencing Ready Reaction Kit. The sample was purified using Multi-Screen HV plate (manufactured by Millipore) in accordance with the manufacture's instruction of Millipore. The thus purified reaction product was stored at −30° C. in the dark.

The dried reaction product was analyzed using ABI PRISM 3700 DNA Analyser (manufactured by PE Biosystems) in accordance with the manufacture's instruction.

The data of about 200,000 reactions obtained by the 3700 DNA Analyser were preserved by transferring into a server (Alpha Server ES40; manufactured by Compaq). The data of about 200,000 reactions corresponded to about 10 times of the genome size.

(5) Assembly

All procedures were carried out based on the UNIX platform. The base call was carried out by phred (The University of Washington), and the vector sequence removal by Cross Match (The University of Washington) and the assembly by phrap (The University of Washington). The contig obtained as the result of assembly was analyzed using a graphical editor consed (The University of Washington). A series of procedures from the base call to assembly were carried out in one lot using a script phredPhrap attached to consed.

(6) Nucleotide Sequence Determination of Gap Region

Each cosmid in the cosmid library constructed in the item (3) was prepared by a method similar to the production method of the double-stranded DNA plasmid described in the item (4-1). The nucleotide sequences of the insertion fragment termini of the cosmid were determined using ABI PRISM BigDye Terminator Cycle Sequencing Ready Reaction Kit (manufactured by PE Biosystems) in accordance with the manufacture's instructions.

Sequencing of both termini of insertion fragments of about 4,000 cosmid clones was carried out, and nucleotide sequences in the shotgun sequencing derived contigs obtained in the item (5) identical to these sequences were screened. By this operation, linkage relationship between each cosmid clone and each contig was revealed and mutual alignment was carried out.

Also, the sequence of a region uncovered by the contig (gap region) was determined by the following method.

Clones containing sequences positioned at contig termini were selected. About 4,000 clones in which only the sequences of one side terminus of insertion fragments were determined were selected from these clones. Subsequently, by identifying whole genome-derived shotgun library clones or cosmid clones in which sequences of respective termini of insertion fragments were contained in two contigs, and by determining full nucleotide sequences of insertion fragments of the clones, the nucleotide sequence of this gap region was determined. In the case of the absence of a shotgun library clone or cosmid clone covering the gap region, the nucleotide sequence of the region was determined by amplifying a DNA fragment of the gap region which was prepared by PCR using primers complementary to the contig termini sequences, and then carrying out the sequencing by a primer walking method using the amplified product as the template or by a shotgun method in which sequence of a shotgun clone prepared from the amplified PCR fragment is determined.

Regarding a region having low sequence accuracy, the sequence accuracy was improved by synthesizing primers making use of the AUTOFINISH function and NAVIGATING function of the consed (The University of Washington), and carrying out the sequence determination by the primer walking method. The nucleotide sequences of the *Streptomyces avermitilis* ATCC 31267 genome determined in this manner are shown in SEQ ID NO:1.

(7) Identification and Function Estimation of ORF

ORFs in the nucleotide sequences shown in SEQ ID NO:1 were identified in the following manner. First, the ORF regions was estimated on the UNIX platform using ORF identification software Glimmer, GeneMark and GeneMark.hmm in accordance with the manual attached to the software. Also, published data on 1,000 ORFs of *Streptomyces coelicolor* A3(2) were used as corresponding learning materials. Based on these results, ORFs in the nucleotide sequences shown in SEQ ID NO:1 were identified.

The function of ORFs was estimated by retrieving homology of the identified ORF nucleotide sequences from amino acid databases such as Swiss-Prot, PIR, GenPept, and the like which are databases of protein coding regions derived from the GenBank database, or by retrieving homology of the identified ORF amino acid sequences from amino acid databases such as Swiss-Prot, PIR, GenPept, and the like which are databases of protein coding regions derived from the GenBank database, using a homology retrieving software BLAST. The ORF nucleotide sequences determined in this manner are shown in SEQ ID NOs:2 to 7552, and the amino acid sequences encoded by the ORFs in SEQ ID NOs:7552 to 15101.

EXAMPLE 2

Screening and Identification of Biosynthetic Gene Cluster of New Polyketide Compound Oligomycin:

(1) Screening of Oligomycin Biosynthetic Gene Cluster

*Streptomyces avermitilis* produces a polyketide compound avermectin having parasiticidal activity and insecticidal activity and also produces other several polyketide compounds. However, there is no information on the presence of the biosynthetic genes, and their distinctive identification has not been accomplished even by carrying out Southern hybridization using a part of the avermectin biosynthetic gene as the probe. By the way, it is known by the analysis of polyketide synthase genes that, among their functional domains, the domains related to β-ketoacyl-ACP synthesis and acyl transfer have high amino acid sequence homology in comparison with other domains (*Science*, 252: 675 (1991), *Proc. Natl. Acad. Sci. USA*, 96: 9509 (1999)).

When BLAST retrieval was carried out on the amino acid sequences of the domains related to β-ketoacyl-ACP synthesis and acyl transfer of the nucleotide sequences of the biosynthetic gene cluster of avermectin produced by *Streptomyces avermitilis* and the nucleotide sequences shown in SEQ ID NO:1, regions considered to be several polyketide synthase genes were found. Among these, two genes having a total length of 60 kb or more were analyzed. When ORF retrieval of the nucleotide sequence shown in SEQ ID NO:15102 was carried out, it was confirmed that seven polyketide synthase genes are encoded in this region. The constitution of domains was also revealed by retrieving homology of deduced amino acid sequences with each domain of the polyketide synthase (FIG. 1). As a result of the domain constitution analysis, it was estimated that 17 modules (domains concerned in the acyl side chain elongation) are present in the deduced seven polyketide synthases and condensation is carried out 16 times. The result coincided with the polyketide skeleton of oligomycin.

(2) Identification of Oligomycin Biosynthetic Gene Cluster

It was considered that the nucleotide sequence shown in SEQ ID NO:15102 contains an oligomycin biosynthetic gene cluster. In order to confirm this, insertion mutation was applied to a region coding for the polyketide synthase by homologous recombination and its influence on the oligomycin production was examined. Among the nucleotide sequence shown in SEQ ID NO:15102, a 3.53 kb BamHI fragment of from the 100,926th base to the 104,455th base of the region considered to encode the polyketide synthase was cut out from a cosmid clone containing a region encoding the polyketide synthase and subcloned into the BamHI site of pUC19. Since the 3,530 bp BamHI fragment contains one BglII site, a 1.95 kb BamHI fragment containing a streptomycin-spectinomycin resistance gene (aad3") was ligated to this site.

The thus ligated product was introduced into *Escherichia coli* DH10B, and the transformant of interest was selected using LA medium containing 0.1 mg/ml ampicillin and 0.1 mg/ml spectinomycin. After extraction of plasmid DNA from the transformant, a 5.48 kb BamHI fragment cloned by digesting with BamHI was cut out and ligated to the BamHI site of pKC7. The ligated product was introduced into *Escherichia coli* DH10B, and the transformant of interest was selected using LA medium containing 0.05 mg/ml kanamycin, 0.1 mg/ml ampicillin and 0.1 mg/ml spectinomycin. Since *Streptomyces avermitilis* restricts DNA methylated with Dam and Dcm, it is necessary to transform *Streptomyces avermitilis* using DNA prepared from *Escherichia coli* from which such methylation had been deleted. Accordingly, plasmid DNA was extracted from the transformant obtained in the above to transform a dam and dcm defective *Escherichia coli* strain GM2929. *Streptomyces avermitilis* was made into protoplasts in the usual way, transformed with the plasmid DNA obtained from the transformant using polyethylene glycol, spread on a regeneration medium and then cultured at 30° C.

Twenty hours after the culturing, soft agar containing 0.1 mg/ml neomycin was layered over the medium in an amount of 2.5 ml per one plate, and transformant were selected by continuing the culturing for 7 days.

Transformants grown on the selection medium were collected, spread on YMS agar medium (4 g/l yeast extract, 10 g/l malt extract, 4 g/l soluble starch, 20 g/l agar, pH 7.5) and cultured at 30° C. for 7 days. Spores formed on the surface were scraped, spread on the YMS agar medium to give a density of 200 colonies per plate and cultured at 30° C. for 5 days.

After confirming formation of spores, colonies were replicated on two media, namely YMS agar plate medium containing 0.1 mg/ml spectinomycin and YMS agar plate medium containing 0.002 mg/ml neomycin and 0.1 mg/ml spectinomycin, and cultured at 30° C. for 5 days.

Among colonies grown on respective plates, homologous recombinants which formed double crossover recombination event showing neomycin sensitivity and spectinomycin resistance were selected.

Recombinants having insertion mutation in the polyketide synthase region, caused by the homologous recombination, were transferred on a production medium (46 g/l glucose, 24 g/l peptonized milk, 2.5 g/l yeast extract, 20 g/l agar, pH 7.5) in a patch shape of 1 square centimeter and cultured at 28° C. for 7 days.

After completion of the culturing, each of the recombinants grown in a patch-shape was hollowed out, and the culture product accumulated in the cells was extracted with 0.5 ml of methanol.

Accumulation of avermectin was observed in the culture product of all recombinants, but oligomycin was not accumulated. Based on the results, it was revealed that the 7 kinds of ORF contained in SEQ ID NO:15102 encode oligomycin biosynthesis enzymes.

EXAMPLE 3

Screening and Identification of Biosynthetic Gene Cluster of New Polyketide Compound Pentaene (1) Screening of Pentaene Biosynthetic Gene Cluster When BLAST retrieval was carried out on the amino acid sequences of the domains related to β-ketoacyl-ACP synthesis and acyl transfer of the nucleotide sequences of the biosynthetic gene cluster of avermectin produced by *Streptomyces avermitilis* and the nucleotide sequences shown in SEQ ID NO:1, regions considered to be several polyketide synthase genes were found.

Among these, one of two gene clusters having a total length of 60 kb or more was found to be an oligomycin biosynthetic gene cluster.

Retrieval of ORF was carried out on the other gene cluster in the same manner as the analysis of oligomycin biosynthetic gene.

Figure 2:
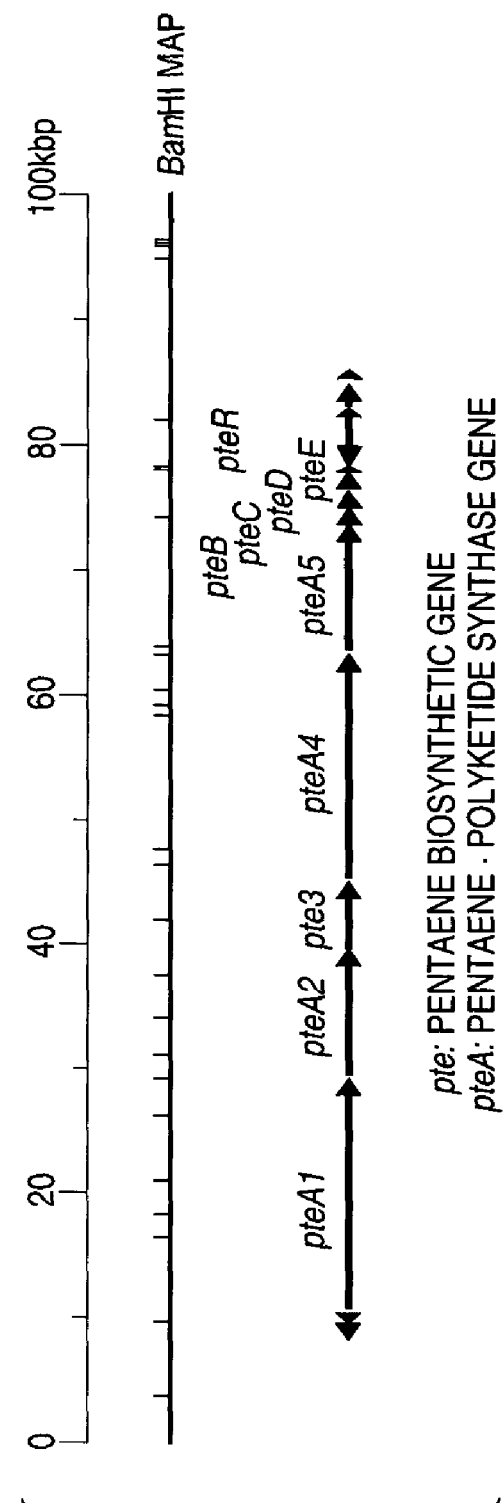
FIG. 2 is a drawing showing the construction of the gene in the region relating to the biosynthesis of pentaene on the genome of *Streptomyces avermitilis* ATCC 31267.
Figure 3:
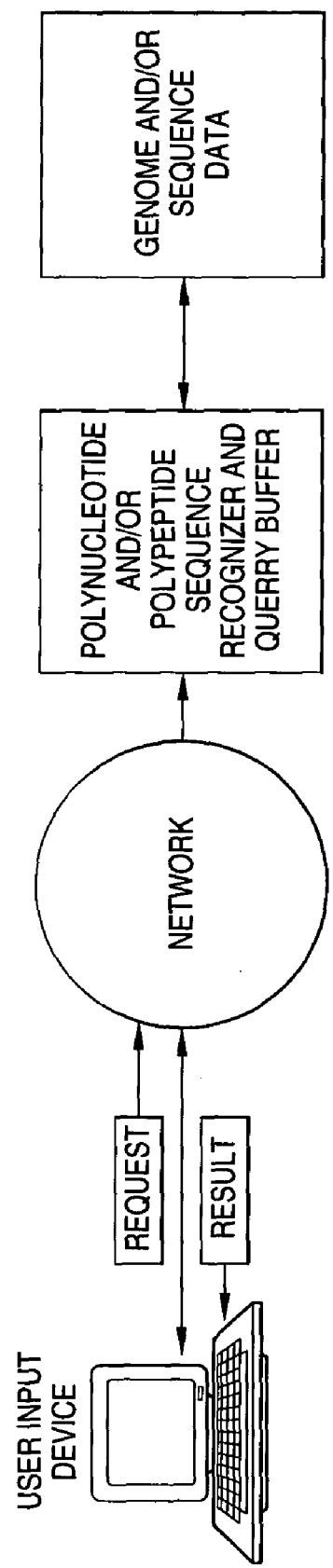
FIG. 3 is a flow chart of an example of a system using the computer readable media according to the present invention.
Figure 4:
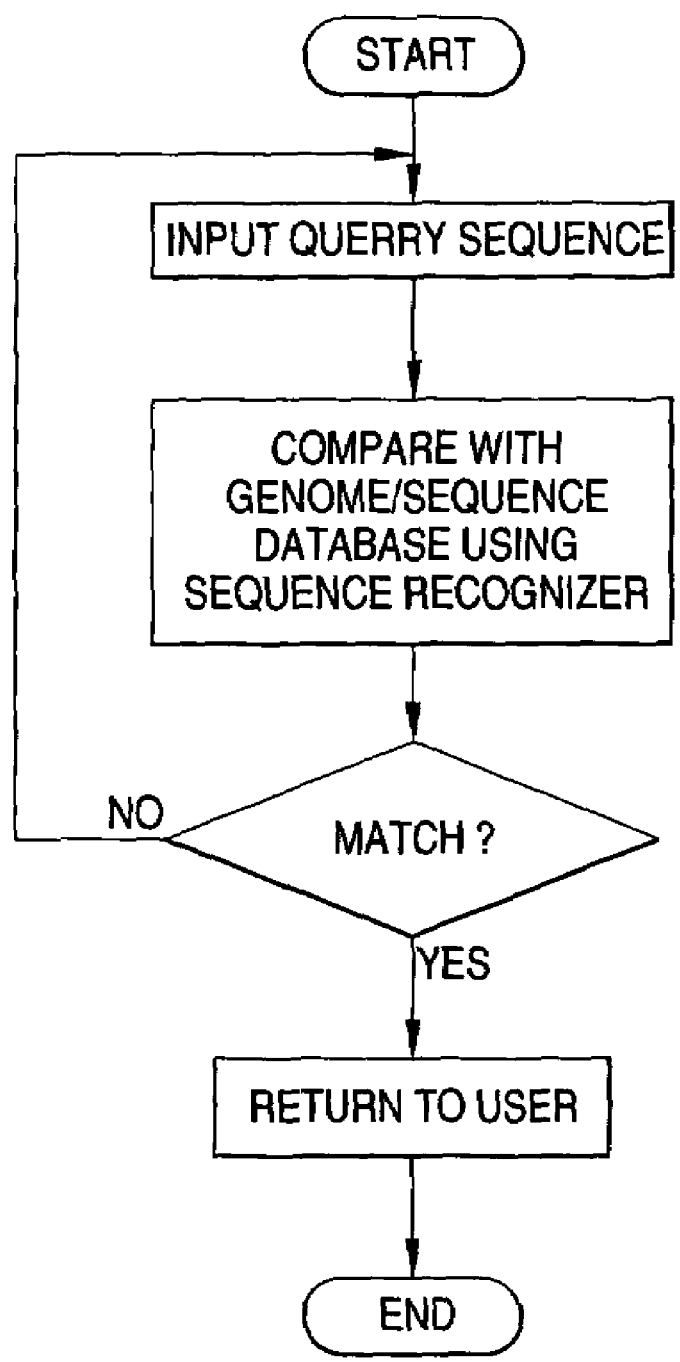
FIG. 4 is a flow chart of an example of a system using the computer readable media according to the present invention.

When ORF retrieval of the nucleotide sequence shown in SEQ ID NO:15103 was carried out, it was confirmed that five polyketide synthase genes are encoded in this region. The constitution of domains was also revealed by retrieving homology of deduced amino acid sequences with each domain of the polyketide synthase (FIG. 2). As a result of the domain constitution analysis, it was estimated that 14 modules are present in the deduced five polyketide synthases and condensation is carried out 13 times. The result coincided with the polyketide skeleton of a pentaene compound, filipin.

(2) Identification of Pentaene Biosynthetic Genes

It was considered that the nucleotide sequence shown in SEQ ID NO:15103 contains a pentaene biosynthetic gene cluster.

In order to confirm this, insertion mutation was applied to a region coding for the polyketide synthase by homologous recombination and its influence on the pentaene production was examined.

Among the nucleotide sequence shown in SEQ ID NO:15103, a 5.56 kb SacI fragment of from the 43,293rd base to the 48,851st base of the region considered to encode the polyketide synthase was cut out from a cosmid clone containing a region encoding the polyketide synthase and subcloned into the SacI site of pUC19. Since the 5.56 kb SacI fragment contains one EcoRV site, a 1.95 kb DraI fragment containing a streptomycin-spectinomycin resistance gene (aad3") was ligated to this site.

The ligated product was introduced into *Escherichia coli* DH10B, and the transformant of interest was selected using LA medium containing 0.1 mg/ml ampicillin and 0.1 mg/ml spectinomycin. After extraction of plasmid DNA from the transformant, a 7.51 kb EcoRI-HindIII fragment cloned by digesting with EcoRI and HindIII was cut out and ligated to the EcoRI/HindIII site of pKC7.

The thus ligated product was introduced into *Escherichia coli* DH10B, and the transformant of interest was selected using LA medium containing 0.05 mg/ml kanamycin, 0.1 mg/ml ampicillin and 0.1 mg/ml spectinomycin.

Since *Streptomyces avermitilis* restricts methylated DNA as described above, plasmid DNA was extracted from the transformant obtained above to transform a dam and dcm defective *Escherichia coli* strain GM2929.

Using methylation-free plasmid DNA obtained from the transformant, *Streptomyces avermitilis* protoplasts were transformed by a polyethylene glycol method, spread on a regeneration medium and then cultured at 30° C.

Twenty hours after the culturing, soft agar containing 0.1 mg/ml neomycin was overcoated on the medium in an amount of 2.5 ml per one plate, and a transformant was selected by continuing the culturing for 7 days.

Transformants grown on the selection medium were collected, spread on YMS agar medium (4 g/l yeast extract, 10 g/l malt extract, 4 g/l soluble starch, 20 g/l agar, pH 7.5) and cultured at 30° C. for 7 days. Spores formed on the surface were scraped, spread on the YMS agar medium to give a density of 200 colonies per plate and cultured at 30° C. for 5 days.

After confirming formation of spores, colonies were replicated on two media, namely YMS agar plate medium containing 0.1 mg/ml spectinomycin and YMS agar plate medium containing 0.002 mg/ml neomycin and 0.1 mg/ml spectinomycin, and cultured at 30° C. for 5 days.

Among colonies grown on respective plates, homologous recombinants which formed double crossover recombination event showing neomycin sensitivity and spectinomycin resistance were selected.

Recombinants having insertion mutation in the polyketide synthase region, caused by the homologous recombination, were transferred on a production medium (40 g/l soluble starch, 20 g/l soybean meal, 0.5 g/l ferrous sulfate heptahydrate, 1 g/l potassium secondary phosphate, 0.3 g/l potassium chloride, 20 g/l agar, pH 6.5) in a patch shape of 1 square centimeter and cultured at 28° C. for 7 days.

After completion of the culturing, each of the recombinants grown in a patch-shape was hollowed out, and the culture product accumulated in the cells was extracted with 0.5 ml of methanol. Accumulation of avermectin was observed in the culture product of all recombinants, but pentaene was not accumulated. Based on the results, it was revealed that the 5 kinds of ORF contained in SEQ ID NO:15103 encode pentaene biosynthesis enzymes.

As is demonstrated by the discovery of biosynthetic genes of new polyketide compounds described above, the present invention provides an effective and quick screening method for discovering a biosynthetic gene cluster of polyketide compounds without using conventional cloning techniques of molecular genetics. In addition, the discovered domain constitution of polyketide synthase also provides useful information for the creation of novel polyketide compounds. This methodology for quick screening of polyketide compounds is an approach which can be carried out efficiently by making use of the genomic nucleotide sequence information disclosed by the present invention, and its effectiveness was found for the first time by the present invention.

EXAMPLE 4

Homologue Retrieval Using *Streptomyces avermitilis* Genome Sequence:

(1) Retrieval of Transketolase

An *Escherichia coli* transketolase sequence (ECTKT) was obtained from Swiss-prot database as the amino acid sequence of a protein whose function as transketolase (EC 2.2.1.1) had been confirmed. Using the full length of the amino acid sequence as the query, homology retrieval was carried out using FASTA program on a nucleotide sequence database of the genome sequences of *Streptomyces avermitilis* or on a database of the amino acid sequences of ORF region deduced from the genome sequences. The presence of significant homology was judged by the E-value of $10^{-10}$ or less.

As a result, significant homology of *Escherichia coli* transketolase ORF was found with the ORF having the nucleotide sequence represented by SEQ ID NO:1755 and the amino acid sequence encoded by the ORF having the nucleotide sequence represented by SEQ ID NO:6292, from the nucleotide sequence database of the genome sequences of *Streptomyces avermitilis* or the database of the amino acid sequences of ORF region deduced from the genome sequences.

In order to examine similarity between the ORF-encoded amino acid sequences and transketolase of other organism species in detail, retrieval was carried out using the amino acid sequences as the query and using BLAST program, on an amino acid sequence database prepared from those which are registered in GenBank (http://www.ncbi.nlm.nih.gov/)nr-aa database, PDB database, Swiss-Prot database, PIR database and PRF database by excluding overlapped parts.

As a result, each of the two amino acid sequences showed significant homology with transketolase of other organism species, and the homology with transketolase was clearly higher than the homology with amino acid sequences of other proteins, so that it was considered that two ORFs encoding a protein having transketolase activity are present in *Streptomyces avermitilis*.

(2) Retrieval of Transaldolase

*Escherichia coli* transketolase sequences TalA (D13159) and TalB (S80045) were obtained from Swiss-prot database as the amino acid sequences of proteins whose function as transaldolase (EC 2.2.1.2) had been confirmed. Using the full length of the amino acid sequences as the query, homology retrieval was carried out using FASTA program on a nucleotide sequence database of the genome sequences of *Streptomyces avermitilis* or on a database of the amino acid sequences of ORF region deduced from the genome sequences. The presence of significant homology was judged by the E-value of $10^{-10}$ or less.

As a result, significant homology of *Escherichia coli* transketolase TalA and TalB ORFs was found with the ORF having the nucleotide sequence represented by SEQ ID NO:1756 and the amino acid sequence encoded by the ORF having the nucleotide sequence represented by SEQ ID NO:6291, from the nucleotide sequence database of the genome sequences of *Streptomyces avermitilis* or the database of the amino acid sequences of ORF region deduced from the genome sequences.

In order to examine similarity between the ORF-encoded amino acid sequences and transketolase of other organism species in detail, retrieval was carried out using the amino acid sequences as the query and using BLAST program, on an amino acid sequence database prepared from those which are registered in GenBank (http://www.ncbi.nlm.nih.gov/)nr-aa database, PDB database, Swiss-Prot database, PIR database and PRF database by excluding overlapped parts.

As a result, both of the two amino acid sequences showed significant homology with transaldolase of other organism species, and the homology with transaldolase was clearly higher than the homology with amino acid sequences of other proteins, so that it was considered that two ORFs encoding a protein having transketolase activity are present in *Streptomyces avermitilis*. Also, the ORF shown by SEQ ID NO:1756 was adjacent to the downstream of ORF shown by SEQ ID NO:1755. On the other hand, the ORF shown by SEQ ID NO:6291 was also adjacent to the downstream of ORF shown by SEQ ID NO:6292.

(3) Retrieval of Glucose-6-Phosphate Dehydrogenase

An *Escherichia coli* glucose-6-phosphate dehydrogenase sequence (accession No. M55005) was obtained from Swiss-prot database as the amino acid sequence of a protein whose function as glucose-6-phosphate dehydrogenase (EC 1.1.1.49) had been confirmed. Using the full length of the amino acid sequence as the query, homology retrieval was carried out using FASTA program on a nucleotide sequence database of the genome sequences of *Streptomyces avermitilis* or on a database of the amino acid sequences of ORF region deduced from the genome sequences. The presence of significant homology was judged by the E-value of $10^{-10}$ or less.

As a result, significant homology of *Escherichia coli* glucose-6-phosphate dehydrogenase ORF was found with the ORF having the nucleotide sequence represented by SEQ ID NO:1757 and the amino acid sequence encoded by the ORF having the nucleotide sequence represented by SEQ ID NO:6290, from the nucleotide sequence database of the genome sequences of *Streptomyces avermitilis* or the database of the amino acid sequences of ORF region deduced from the genome sequences.

In order to examine similarity between the ORF-encoded amino acid sequences and transketolase of other organism species in detail, retrieval was carried out using the amino acid sequences as the query and using BLAST program, on an amino acid sequence database prepared from those which are registered in GenBank (http://www.ncbi.nlm.nih.gov/)nr-aa database, PDB database, Swiss-Prot database, PIR database and PRF database by excluding overlapped parts.

As a result, each of the two amino acid sequences showed significant homology with glucose-6-phosphate dehydrogenase of other organism species, and the homology with glucose-6-phosphate dehydrogenase was clearly higher than the homology with amino acid sequences of other proteins, so that it was considered that proteins having amino acid sequences encoded by the two ORFs function as glucose-6-phosphate dehydrogenase. Based on the results, it was considered that two ORFs encoding a protein having glucose-6-phosphate dehydrogenase activity are present in *Streptomyces avermitilis*. Also, the ORF shown by SEQ ID NO:1756 was adjacent to the downstream of ORF shown by SEQ ID NO:1755. On the other hand, the ORF shown by SEQ ID NO:6290 was also adjacent to the downstream of ORF shown by SEQ ID NO:6291.

Based on these results, it was revealed that the ORF shown by SEQ ID NO:1755, the ORF shown by SEQ ID NO:1756 and the ORF shown by SEQ ID NO:1757 form an operon, and the ORF shown by SEQ ID NO:6292, the ORF shown by SEQ ID NO:6291 and the ORF shown by SEQ ID NO:6290 also form an operon.

EXAMPLE 5

Screening of New Secondary Metabolite Biosynthetic Gene Clusters:

It is known that the genus *Streptomyces* produces a great variety of secondary metabolites. Based on their biosynthetic pathway, the secondary metabolites can be classified into melanin, β-lactam, peptide, aminoglycoside, aromatic polyketide (containing an aromatic ring such as tetracycline, quinone and anthracycline), macrolide (including large ring lactone and lactam), shikimic acid, terpene, siderophore compounds and the like. Melanin compounds are formed by condensation of aromatic amino acid metabolites. β-Lactam and peptide compounds are formed by condensation of amino acids by a nonribosomal peptide synthetase without peptide elongation by a ribosome. Aminoglycoside antibiotics are formed by glycosidation of saccharide and aminocyclitol. Aromatic polyketide compounds are formed from acetic acid or malonic acid via condensation, dehydration and cyclization with type II polyketide synthase. Large ring lactones (including lactam) such as macrolide and the like are formed from a lower fatty acid such as acetic acid or propionic acid or a dicarboxylic acid thereof via a reaction such as condensation or the like with type I polyketide synthase, followed by cyclization to form lactone or lactam. Shikimic acid compounds are formed by metabolism of an aromatic amino acid. Terpene compounds are formed by condensation of isoprenoid-2-phosphate. Also, siderophore compounds are formed by binding of succinic acid and diaminocarboxylic acid.

When BLAST retrieval of amino acid sequences of the already reported secondary metabolite biosynthetic enzymes and the nucleotide sequences shown in SEQ ID NO:1 was carried out, 27 regions considered to be secondary metabolite biosynthetic gene clusters were found in addition to those of avermectin, oligomycin and polyene compounds. Details of the 27 gene groups were 4 gene clusters relating to the formation of melanins (including aromatic melanin), 5 gene cluster relating to the formation of terpene compounds, 1 gene cluster relating to siderophore formation, 6 gene clusters relating to the formation of polyketide lactone or lactam compounds (type I polyketide synthase is related), 2 gene clusters relating to the formation of aromatic polyketide compounds (type II polyketide synthase is related), 1 gene cluster relating to the formation of other polyketide compounds (polyketide synthase other than the type I and type II polyketide synthases is related), and 8 gene clusters relating to the formation of peptide compounds (nonribosomal peptide synthetase is related). The sequences contained in respective gene clusters are shown below.

(1) Gene Clusters Relating to the Formation of Melanin Compounds
  i) The ORFs shown in SEQ ID NOs:1125 and 1126 were present in the Mel1 (tyrosinase related) region.
  ii) The ORFs shown in SEQ ID NOs:5345 and 5346 were present in the Mel2 (tyrosinase related) region.
  iii) The ORFs shown in SEQ ID NOs:5133 and 5134 were present in the Hpd (hydroxylphenylpyruvate dioxygenase related) region.
  iv) The ORFs shown in SEQ ID NOs:2821 to 2830 were present in the Spp (type II polyketide synthase related) region.

(2) Gene Clusters Relating to the Formation of Terpene Compounds
  i) The ORFs shown in SEQ ID NOs:1008 to 1014 were present in the Crt region.
  ii) The ORF shown in SEQ ID NO:77 was present in the Terp region.
  iii) The ORFs shown in SEQ ID NOs:1638 to 1643 were present in the Shr region.
  iv) The ORFs shown in SEQ ID NOs:2151 to 2153 were present in the Geo region.
  v) The ORFs shown in SEQ ID NOs:2986 to 2988 were present in the Ptc region.

(3) Gene Clusters Relating to the Formation of Siderophore Compounds
  i) The ORFs shown in SEQ ID NOs:5252 to 5256 were present in the Sdf region.

(4) Gene Clusters Relating to the Formation of Polyketide Lactone (or Lactam) Compounds
  i) The ORFs shown in SEQ ID NOs:7337 to 7341 were present in the Pks-1 region.
  ii) The ORFs shown in SEQ ID NOs:1539 to 1542 were present in the Pks-2 region.
  iii) The ORFs shown in SEQ ID NOs:2263 to 2272 were present in the Pks-3 region.
  iv) The ORFs shown in SEQ ID NOs:7163 to 7168 were present in the Pks-4 region.
  v) The ORFs shown in SEQ ID NOs:2353 to 2356 were present in the Pks-5 region.
  vi) The ORFs shown in SEQ ID NOs:101 and 102 were present in the Pks-11 region.

(5) Gene Clusters Relating to the Formation of Aromatic Polyketide Compounds
i) The ORFs shown in SEQ ID NOs:3637 to 3653 were present in the Pks-8 region.
ii) The ORFs shown in SEQ ID NOs:2359 to 2376 were present in the Pks-9 region.

(6) Gene Clusters Relating to the Formation of Polyketide Compounds Biologically Synthesized with a Synthase Other Than Type I and Type II Polyketide Synthases
i) The ORFs shown in SEQ ID NOs:7109 and 7110 were present in the Pks-10 region.

(7) Gene Clusters Relating to the Formation of Peptide Compounds
i) The ORFs shown in SEQ ID NOs:3179 to 3190 were present in the Nrps-1 region.
ii) The ORFs shown in SEQ ID NOs:3621 to 3635 were present in the Nrps-2 region.
iii) The ORFs shown in SEQ ID NOs:3143 to 3152 were present in the Nrps-3 region.
iv) The ORFs shown in SEQ ID NOs:7142 to 7145 were present in the Nrps-4 region.
v) The ORFs shown in SEQ ID NOs:6586 to 6611 were present in the Nrps-5 region.
vi) The ORFs shown in SEQ ID NOs:595 to 603 were present in the Nrps-6 region.
vii) The ORFs shown in SEQ ID NOs:825 to 859 were present in the Nrps-7 region.
viii) The ORFs shown in SEQ ID NOs:1238 to 1241 were present in the Nrps-8 region.

Among the ORFs of the gene clusters relating to the formation of polyketide lactone (or lactam) compounds by type I polyketide synthase and the gene clusters relating to the formation of peptide compounds, the regions encoding a polyketide synthase and a nonribosomal peptide synthetase are considered to be multifunctional polypeptides. It is possible to estimate functional domains existing in the polypeptides by examining consensus sequences of respective functional domains of the polyketide synthase and nonribosomal peptide synthetase (*Science*, 252: 675 (1991), *Pro. Natl. Acad. Sci. USA*, 96: 9509 (1999), *Chem. & Biol.*, 6: 493 (1999)). Functional domains of ORF estimated to be a polyketide synthase are shown in Table 1, and functional domains of ORF estimated to be a nonribosomal peptide synthetase and deduced amino acids to be activated are shown in Table 2.

TABLE 1

Functional domain constitution of type I polyketide synthase

| Peptide | Module | Functional domain | | | | | |
|---|---|---|---|---|---|---|---|
| Pks-1_1 | Module 1 | KS | AT | | | ACP | KR |
| Pks-1_2 | Module 2 | KS | AT | | | | |
| Pks-2 | Module 1 | KS | AT | DH | KR | ACP | |
| | Module 2 | KS | AT | DH | KR | ACP | TE |
| Pks-3_1 | Loading Module | KS* | AT | | | ACP | |
| Pks-3_2 | Module 1 | | | | KR | ACP | |
| Pks-4 | Module 1 | KS | AT | | KR | ACP | |
| Pks-5 | Loading Module | KS* | AT | | | ACP | |
| | Module 1 | KS | AT | DH | KR | ACP | |
| | Module 2 | KS | AT | DH | KR* | ACP | |
| Pks-6 | Module 1 | KS | AT | | | ACP | |
| Pks-7 | Module 1 | KS | | | | ACP | |

Description of abbreviations of functional domains:
ACP: acyl carrier protein
AT: acyl transferase
DH: dehydrogenase
KR: β-ketoacyl-ACP reductase
KS: β-ketoacyl-ACP synthase
TE: thioesterase The remark * indicates that the domain is considered to not function due to substitution or deletion of amino acid in the consensus sequence region.

TABLE 2

Consensus sequence of amino acid adenylylation domain of nonribosomal peptide synthetase and activated amino acid and domain constitution

| Peptide | Consensus sequence of adenylylation domain* | | | | | | | | Estimated substrate | Domain Constitution*** |
|---|---|---|---|---|---|---|---|---|---|---|
| | 235 | 236 | 239 | 278 | 299 | 301 | 322 | 330 | | |
| Nrps-1_1 | D | F | W | N | V | G | M | V | Threonine | C-A-T |
| Nrps-1_2 | D | A | W | L | L | G | A | V | Leucine | C-A-T-E |
| Nrps-1_3 | D | V | W | H | V | S | L | L | Serine | A-T |
| | D | G | T | L | T | A | E | V | Tyrosine | C-A-T |
| Nrps-2_1 | D | A | Q | E | L | A | V | L | Glutamine | A-T |
| Nrps-2_2 | D | A | W | L | Y | G | L | V | Leucine | C-A-T-E |
| | D | L | P | K | V | G | E | V | Asparagine | C-A-T |
| Nrps-2_3 | D | V | W | N | L | S | L | I | Serine | C-A-T-E |
| | D | L | P | K | V | G | E | V | Asparagine | C-A-T-E |
| | D | L | P | K | V | G | E | V | Asparagine | C-A-T-Te |
| Nrps-3_1 | D | M | E | L | L | G | L | I | Ornithine | C-A-T |
| Nrps-3_2 | nd | nd | nd | nd | nd | nd | nd | nd** | | E-Te |
| Nrps-3_3 | D | V | W | H | V | S | L | V | Serine | A-T |
| Nrps-4 | D | L | T | K | L | G | E | V | Asparagine | A-T |
| Nrps-5 | D | V | Q | L | L | A | H | V | Proline | A-T |
| Nrps-6 | D | V | Q | L | I | A | H | V | Proline | A-T |
| Nrps-7_1 | D | F | E | T | T | A | A | V | Valine | A-T |
| Nrps-7_2 | D | A | K | D | L | G | V | V | Glutamic acid | A |
| Nrps-7_3 | D | F | Q | L | L | G | L | A | Pipecolic acid | A-T |
| Nrps-7_4 | D | A | F | W | L | G | G | T | Valine | A-T-C |
| Nrps-7_5 | D | A | Q | D | L | G | L | V | Glutamic acid | A-T |

TABLE 2-continued

Consensus sequence of amino acid adenylylation domain
of nonribosomal peptide synthetase
and activated amino acid and domain constitution

| Peptide | Consensus sequence of adenylylation domain* | | | | | | | | Estimated substrate | Domain Constitution*** |
|---|---|---|---|---|---|---|---|---|---|---|
| | 235 | 236 | 239 | 278 | 299 | 301 | 322 | 330 | | |
| Nrps-7_6 | D | F | Q | L | V | G | V | A | Pipecolic acid | C-A-T |
| Nrps-7_7 | D | V | W | H | V | T | V | V | Serine | A-T |
| Nrps-7_8 | nd | nd | nd | nd | nd | nd | nd | nd** | — | T-C |
| Nrps-7_9 | nd | nd | nd | nd | nd | nd | nd | nd** | — | C |
| Nrps-7_10 | nd | nd | nd | nd | nd | nd | nd | nd** | — | C |
| Nrps-7_11 | D | L | Y | N | L | S | L | I | Cysteine | A-T |
| Nrps-7_12 | nd | nd | nd | nd | nd | nd | nd | nd** | — | T-C-T-Te |
| Nrps-7_13 | nd | nd | nd | nd | nd | nd | nd | nd** | — | T-C |
| Nrps-8 | D | L | V | F | G | L | G | I | Alanine | A |
| Nrps-9 | D | H | E | S | D | V | G | I | Cysteine | A |

*Numbers from the N-terminal terminal, based on the amino acid sequence from Grs (gramicidin synthetase) nonribosomal peptide synthetase adenylylation domain.
**Known consensus sequence cannot be found or no adenylylation domain exists.
***Description of abbreviations of functional domains:
C: condensing enzyme
T: peptide carrier protein
Te: thioesterase
A: adenylylation enzyme
E: transferase

EXAMPLE 6

Retrieval of Genes Effective in Improving Avermectin Production and Reconstruction of Avermectin Productivity-Improved Strain Based on Genome Information:

(1) Retrieval of Genes Effective in Improving Avermectin Production

S. avermitilis ATCC 31267 (wild strain) and an avermectin-high-producing mutant obtained from the wild strain by repeating many steps of random mutation and selection using a mutagen N-methyl-N'-nitro-N-nitrosoguanidine were cultured using an avermectin production medium, and intracellular proteins and the full RNA of transcription products 24 hours and 48 hours thereafter were compared. As a result, it was observed that the transcription quantity of some mRNA's was different, and when the result was confirmed once more by changing the production medium, it was revealed that the expression quantity was changed in two genes among them. When partial sequences of cDNA fragments of the two mRNA's were examined, they were SEQ ID NO:3692 and SEQ ID NO:923. The ORF of SEQ ID NO:923 was identified as a regulator gene existing in the avermectin biosynthetic gene cluster. On the other hand, SEQ ID NO:3692 was a novel ORF. Since the mRNA corresponding to SEQ ID NO:3692 was detected only in a small amount from the avermectin-high-producing strain, it was considered that the gene product of the ORF is a repressor for avermectin production in S. avermitilis.

(2) Reconstruction of Avermectin High Production Strain

It was considered that production of avermectin was increased in the avermectin high production mutant obtained from S. avermitilis ATCC 31267 by repeating many steps of random mutation and selection using a mutagen N-methyl-N'-nitro-N-nitrosoguanidine, due to reduced expression of the gene product of ORF as a repressor shown in SEQ ID NO:3692. Thus, improvement of avermectin production can be expected by disrupting the ORF represented by SEQ ID NO:3692 in the wild strain.

The ORF moiety shown in SEQ ID NO:3692 and its upstream and downstream moieties were amplified by PCR from the chromosomal DNA of S. avermitilis ATCC 31267 to produce a DNA fragment in which a resistance gene was arranged in almost the center of the ORF, and a disruption strain was produced by allowing the fragment to cause homologous recombination with the same region of the chromosome of the wild strain. For the amplification of the upstream side of ORF of SEQ ID NO:3692, primer 1 (5'-CTCGAGGATCCGAGCGCTTCAG-CACGTCGGAGATGGTT-3'; SEQ ID NO:15106) and primer 2 (5'-CTCGAGAAGCTTCACCCAGATCACCAG-GTTGTCGCCCTCG-3'; SEQ ID NO:15107) were used and the chromosomal DNA of S. avermitilis ATCC 31267 was used as the template, and 0.2 U of Expand Taq DNA polymerase (manufactured by Boehringer-Mannheim) was added thereto in the presence of dATP, dGTP, dCTP and dTTP to carry out denaturation at 96° C. for 5 minutes, followed by 30 cycles of the reaction, 1 cycle of the reaction at 98° C. for 15 seconds and at 70° C. for 60 seconds, to thereby amplify a fragment of 1861 bp. On the other hand, for the amplification of the downstream side of ORF of SEQ ID NO:3692, primer 3 (5'-CTCGAGAAGCTTGGAGCCGTACCCGT-TGACGATGAAGGACC-3'; SEQ ID NO:15108) and primer 4 (5'-CTCGAGGATCCATCTGATGCCGTCCT-TCGCCATGCC-3'; SEQ ID NO:15109) were used and the chromosomal DNA of S. avermitilis ATCC 31267 was used as the template, and 0.2 U of Expand Taq DNA polymerase (manufactured by Boehringer-Mannheim) was added thereto in the presence of DATP, dGTP, dCTP and dTTP to carry out denaturation at 96° C. for 5 minutes, followed by 30 cycles of the reaction, 1 cycle of the reaction at 98° C. for 15 seconds and at 70° C. for 60 seconds, to thereby amplify a fragment of 1656 bp. Each of the amplified fragments was digested with BamHI and HindIII, the 2 fragments were mixed with pUC19 which had been digested with HindIII, and T4 DNA polymerase and ATP were added thereto to ligate the 3 fragments. The thus ligated product was introduced into Escherichia coli DH10B, and the transformant of interest was selected using LA medium containing 0.1 mg/ml ampicillin. A plasmid DNA was extracted from the transformant, partially digested with BamHI and further ligated to a BamHI fragment of 1.95 kb containing a streptomycin-spectinomycin resistance gene (aad3"). The ligated product was introduced into *Escherichia coli* DH10B, and transformants were selected using LA medium containing 0.1 mg/ml ampicillin and 0.1 mg/ml spectinomycin. A recombinant plasmid was extracted from each transformant and digested with EcoRI/HindIII to select a clone in which the streptomycin-spectinomycin resistance gene (aad3") was arranged not in the BamHI cloning site of the vector but in the center of the cloned fragment. A plasmid DNA was extracted from the transformant of interest, a HindIII fragment of 5.47 kb which had been cloned by digesting with HindIII was cut out and ligated to the HindIII site of pKC7. The thus ligated product was introduced into *Escherichia coli* DH10B, and the transformant of interest was selected using LA medium containing 0.05 mg/ml kanamycin, 0.1 mg/ml ampicillin and 0.1 mg/ml spectinomycin. Since *Streptomyces avermitilis* restricts methylated DNA as described above, a plasmid DNA was extracted from the transformant obtained above to transform a dam and dcm defective *Escherichia coli* GM2929. Using a methylation-free plasmid DNA obtained from the transformant, protoplasts of *Streptomyces avermitilis* ATCC 31267 were transformed by a polyethylene glycol method, spread on a regeneration medium and then cultured at 30° C. Twenty hours after the culturing, soft agar containing 0.1 mg/ml neomycin was layered over the medium in an amount of 2.5 ml per one plate, and a transformant was selected by continuing the culturing for 7 days. Transformants grown on the selection medium were collected, spread on YMS agar medium (4 g/l yeast extract, 10 g/l malt extract, 4 g/l soluble starch, 20 g/l agar, pH 7.5) and cultured at 30° C. for 7 days. Spores formed on the surface were scraped, spread on the YMS agar medium to give a density of 200 colonies per plate and cultured at 30° C. for 5 days.

After confirming formation of spores, colonies were replicated on two media, namely YMS agar plate medium containing 0.1 mg/ml spectinomycin and YMS agar plate medium containing 0.002 mg/ml neomycin and 0.1 mg/ml spectinomycin, and cultured at 30° C. for 5 days. Among colonies grown on respective plates, homologous recombinants which formed double crossover recombination event showing neomycin sensitivity and spectinomycin resistance were selected. Each of the recombinants having insertion mutation in the chromosomal ORF shown by SEQ ID NO:3692, caused by homologous recombination, was inoculated into a 100 ml-conical flask containing 10 ml of a production medium (46 g/l glucose, 24 g/l peptonized milk, 2.5 g/l yeast autolysate, pH 7.5) and cultured at 28° C. for 7 days under shaking.

After completion of the culturing, 10 ml of methanol was added thereto, followed by shaking for 30 minutes to extract the cultured product. The cell residue was removed by centrifugation at 3,000 rpm for 5 minutes to obtain supernatant. Amount of avermectin contained in the supernatant was determined using an ODS column (4.6φmm×250 mm; moving bed, methanol:water=80:20). It was found that about 5 μg/ml avermectin was accumulated in *S. avermitilis* ATCC 31267, while about 28 μg/ml avermectin was accumulated in the recombinant in which the ORF shown in SEQ ID NO:3692 had been disrupted.

As is demonstrated by the reconstruction of avermectin productivity-improved strain, the present invention provides an effective and novel breeding method for obtaining industrially advantageous strains by excluding disadvantages of conventional mutation breeding. The methodology for reconstructing producer strains by reconstructing effective mutation is an approach which can be carried out efficiently by using the genomic nucleotide sequences disclosed by the present invention, and its effectiveness was found for the first time by the present invention.

While the invention has been described in detail and with reference to specific embodiments thereof, it will be apparent to one of skill in the art that various changes and modifications can be made therein without departing from the spirit and scope thereof. All references cited herein are incorporated in their entirety.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07630836B2). An electronic copy of the "Sequence Listing" will also be available from the USPTO upon request and payment of the fee set forth in 37 CFR 1.19(b)(3).

What is claimed is:

1. A method for identifying a genomic polynucleotide which is concerned with biosynthesis of an antibiotic and is homologous to a gene derived from an actinomycetes, said method comprising:
   (a) incubating a polynucleotide array with a labeled genomic polynucleotide, under hybridization conditions, said polynucleotide array comprising a solid support adhered to at least two of the following groups of polynucleotides (1), (2) and (3): (1) first polynucleotides comprising the nucleotide sequence represented by SEQ ID NO:415, (2) second polynucleotides which are 80% homologous to the first polynucleotides and which encode a polyketide synthase, and (3) third polynucleotides comprising a sequence of 10 to 200 continuous bases of the first or second polynucleotides, wherein at least one polynucleotide on the array is selected from a different group from that of other polynucleotides on the array
   (b) detecting any hybridization of said genomic polynucleotides to said array, and
   (c) determining whether hybridized genomic polynucleotides of step (b) are concerned with biosynthesis of an antibiotic and are homologous to a gene derived from an actinomycetes.

2. The method according to claim 1, wherein the actinomycetes is a microorganism belonging to the genus *Streptomyces*, the genus *Streptosporangium*, the genus *Amycolatop-*

*sis*, the genus *Actinoplanes*, the genus *Nocardioides*, the genus *Pseudonocardia*, the genus *Actinobispora*, the genus *Saccharomonospora*, the genus *Saccharopolyspora*, the genus *Saccharothrix*, the genus *Actinopolyspora*, the genus *Actinomadura*, the genus *Microbispora*, the genus *Microtetraspora*, the genus *Thermomonospora*, or the genus *Micromonospora*.

3. The method according to claim 2, wherein the microorganism belonging to the genus *Streptomyces* is *Streptomyces avermitilis*.

4. The method according to claim 1, wherein the labeled genomic polynucleotide is derived from *Escherichia coli*.

5. The method according to claim 1, wherein said antibiotic is polyketide.

6. The method according to claim 1, wherein said labeled genomic polynucleotide is a labeled actinomycetes genomic polynucleotide.

7. The method according to claim 1, wherein said labeled genomic polynucleotide is a labeled mutant actinomycetes genomic polynucleotide.

* * * * *